US011147689B2

United States Patent
Nic

(10) Patent No.: US 11,147,689 B2
(45) Date of Patent: Oct. 19, 2021

(54) ACETABULAR CUP REMOVER WITH INDEXING ASSEMBLY FOR ROTATING THE REMOVAL BLADE AROUND THE CUP

(71) Applicant: Stryker Corporation, Kalamazoo, MI (US)

(72) Inventor: David M. Nic, Vicksburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 192 days.

(21) Appl. No.: 16/594,219

(22) Filed: Oct. 7, 2019

(65) Prior Publication Data

US 2020/0030117 A1  Jan. 30, 2020

Related U.S. Application Data

(63) Continuation of application No. 14/834,662, filed on Aug. 25, 2015, now Pat. No. 10,463,507, which is a
(Continued)

(51) Int. Cl.
*A61F 2/46* (2006.01)
*A61B 17/14* (2006.01)
*A61B 17/16* (2006.01)

(52) U.S. Cl.
CPC .......... *A61F 2/4609* (2013.01); *A61B 17/142* (2016.11); *A61B 17/1637* (2013.01);
(Continued)

(58) Field of Classification Search
CPC ............ A61F 2/4609; A61F 2002/4619; A61F 2002/4623; A61F 2002/4624; A61F 2002/4625; A61F 2002/4627; A61F 2002/4628; A61F 2002/469; A61B 17/142; A61B 17/1637; A61B 17/1642; A61B 17/1666
See application file for complete search history.

(56) References Cited

U.S. PATENT DOCUMENTS 2,505,917 A    5/1950  Schumacher
3,943,916 A  * 3/1976  Vadas .............. A61B 17/32053
                                                         600/564
(Continued)

FOREIGN PATENT DOCUMENTS

DE    8715836 U1   6/1988
DE    9413940 U1  11/1994
(Continued)

OTHER PUBLICATIONS

International Search Report for International Patent Application No. PCT/US2013/028535 completed Aug. 9, 2013, dated Sep. 8, 2013; 3 pages.
(Continued)

*Primary Examiner* — Kevin T Truong
*Assistant Examiner* — Tracy L Kamikawa
(74) *Attorney, Agent, or Firm* — Howard & Howard Attorneys PLLC

(57) ABSTRACT

An acetabular cup remover with a blade for removing tissue adjacent an acetabular cup. The blade is oscillated against an arcuate section of tissue. Once a section of tissue is cut, an indexing assembly rotates the blade. The blade is again oscillated to cut a new arcuate section of tissue.

12 Claims, 20 Drawing Sheets

Related U.S. Application Data continuation of application No. PCT/US2013/028535, filed on Mar. 1, 2013.

(52) U.S. Cl.
CPC .... *A61B 17/1666* (2013.01); *A61F 2002/469* (2013.01); *A61F 2002/4619* (2013.01); *A61F 2002/4627* (2013.01); *A61F 2002/4628* (2013.01)

(56) References Cited

U.S. PATENT DOCUMENTS

| | | |
|---|---|---|
| 4,271,849 A | 6/1981 | Rehder |
| 4,802,468 A | 2/1989 | Powlan |
| 5,112,338 A | 5/1992 | Anspach, III |
| 5,171,277 A | 12/1992 | Roger |
| 5,290,315 A | 3/1994 | DeCarlo, Jr. |
| 5,431,657 A | 7/1995 | Rohr |
| 6,013,082 A | 1/2000 | Hiernard et al. |
| 6,132,469 A | 10/2000 | Schroeder |
| 6,565,575 B2 | 5/2003 | Lewis |
| 7,763,031 B2 * | 7/2010 | Tulkis .................. A61F 2/4609 606/99 |
| 7,998,146 B2 | 8/2011 | Anderson |
| 8,034,059 B2 | 10/2011 | Tulkis |
| 2002/0116007 A1 | 8/2002 | Lewis |
| 2004/0153080 A1 | 8/2004 | Dong et al. |
| 2006/0200165 A1 | 9/2006 | Tulkis |
| 2007/0021766 A1 | 1/2007 | Belagali et al. |
| 2008/0195111 A1 | 8/2008 | Anderson |
| 2012/0184964 A1 | 7/2012 | Hudak, Jr. et al. |
| 2015/0359641 A1 | 12/2015 | Nic |

FOREIGN PATENT DOCUMENTS

| | | |
|---|---|---|
| EP | 0140642 B1 | 6/1988 |
| EP | 0427754 B1 | 2/1995 |
| EP | 0860143 A2 | 8/1998 |
| EP | 0931523 A1 | 7/1999 |
| EP | 0951872 A2 | 10/1999 |
| FR | 2682288 A1 | 4/1993 |
| GB | 2299758 A | 10/1996 |
| SU | 1664294 A1 | 7/1991 |
| WO | 2012099790 A1 | 7/2012 |

OTHER PUBLICATIONS

Grigoris, P. et al., "A Technique for Removing an Intrapelvic Acetabular Cup", J Bone Joint Surg [Br], vol. 75-B, 1993, pp. 25-27.
Sandiford, Nemandra A., "Revision of the Well Fixed Birmingham Hip Resurfacing Acetabular Component—Results Using a Novel Device", Acta Orthop. Belg., vol. 78, 2012, pp. 49-54.
Machine-assisted English translation for DE 87 15 836 extracted from espacenet.com database on Dec. 4, 2017, 11 pages.
Machine-assisted English translation for DE 94 13 940 extracted from espacenet.com database on Dec. 4, 2017, 15 pages.
English language abstract for EP 0 427 754 extracted from espacenet.com database on Dec. 4, 2017, 2 pages.
English language abstract and machine-assisted English translation for EP 0 931 523 extracted from espacenet.com database on Dec. 4, 2017, 13 pages.
English language abstract and machine-assisted English translation for FR 2 682 288 extracted from espacenet.com database on Dec. 4, 2017, 7 pages.
Partial machine-assisted English translation for SU 1664294 extracted from espacenet.com database on Dec. 4, 2017, 2 pages.
Stryker, "Stryker Ezout Procedural Video HD", https://vimeo.com/230726519, Aug. 23, 2017, 1 page.

* cited by examiner

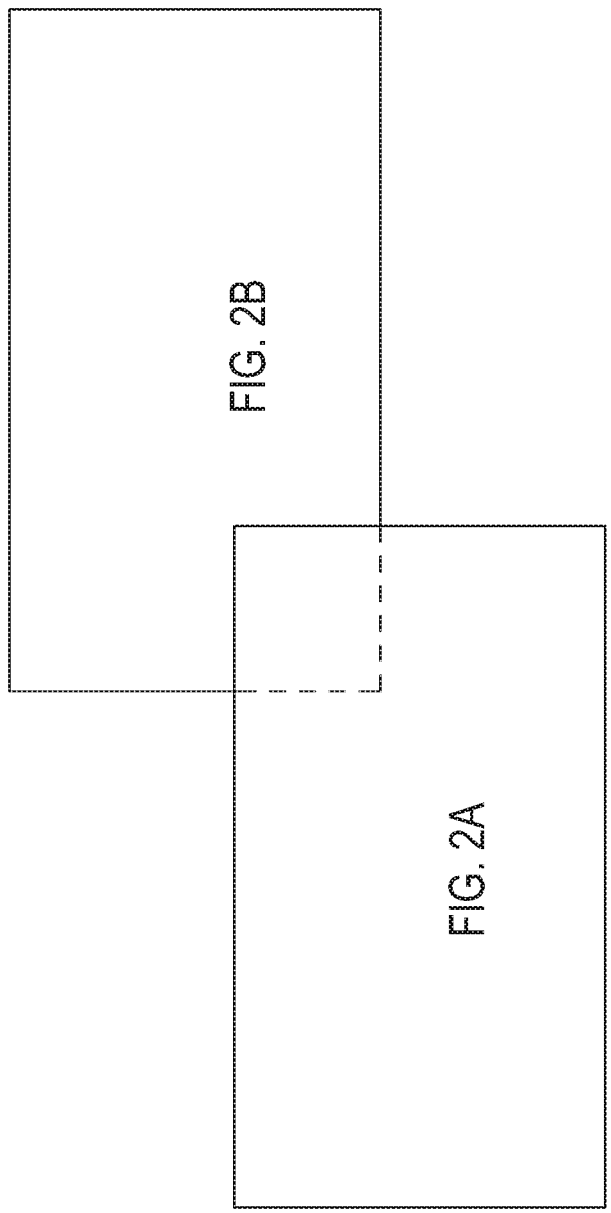

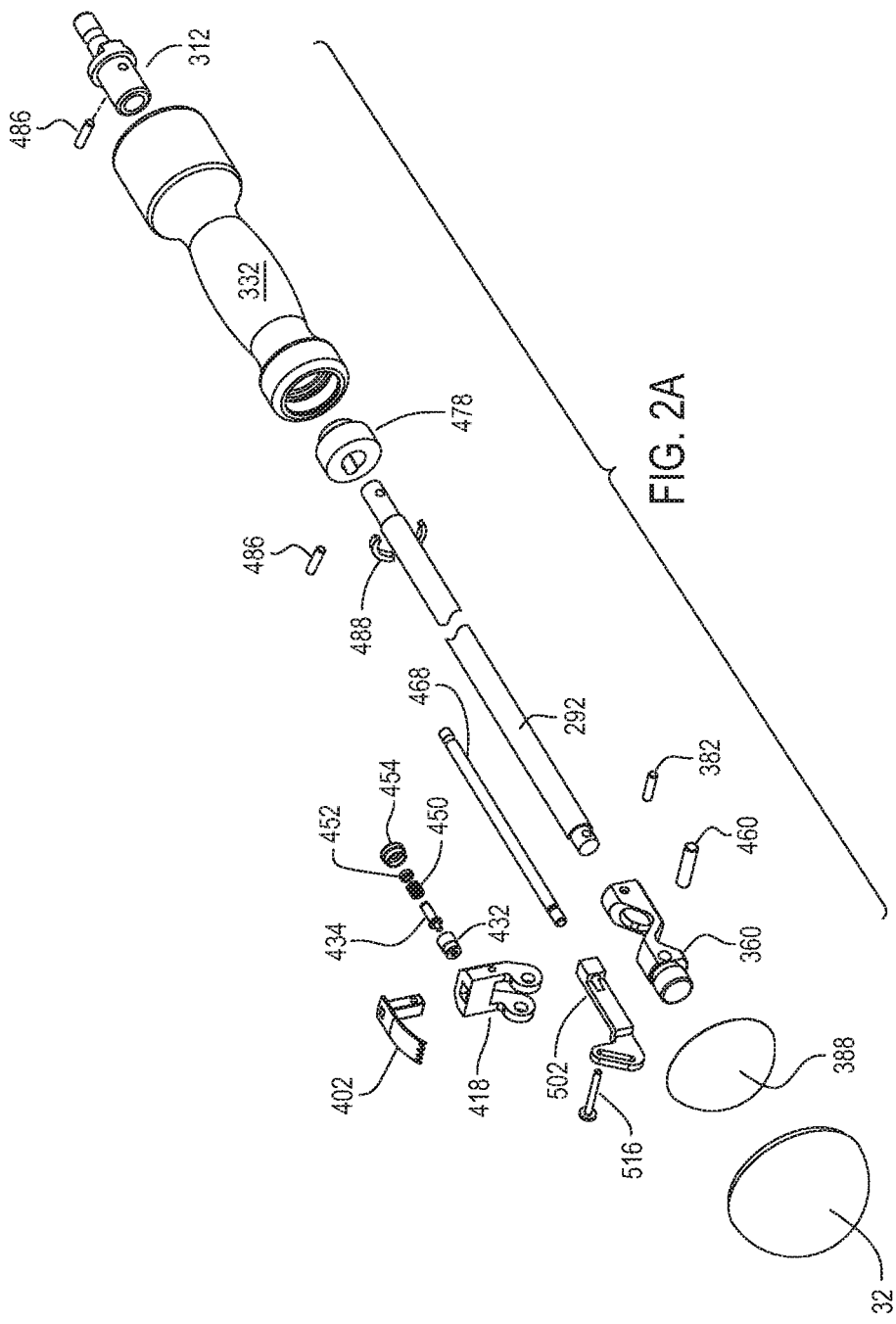

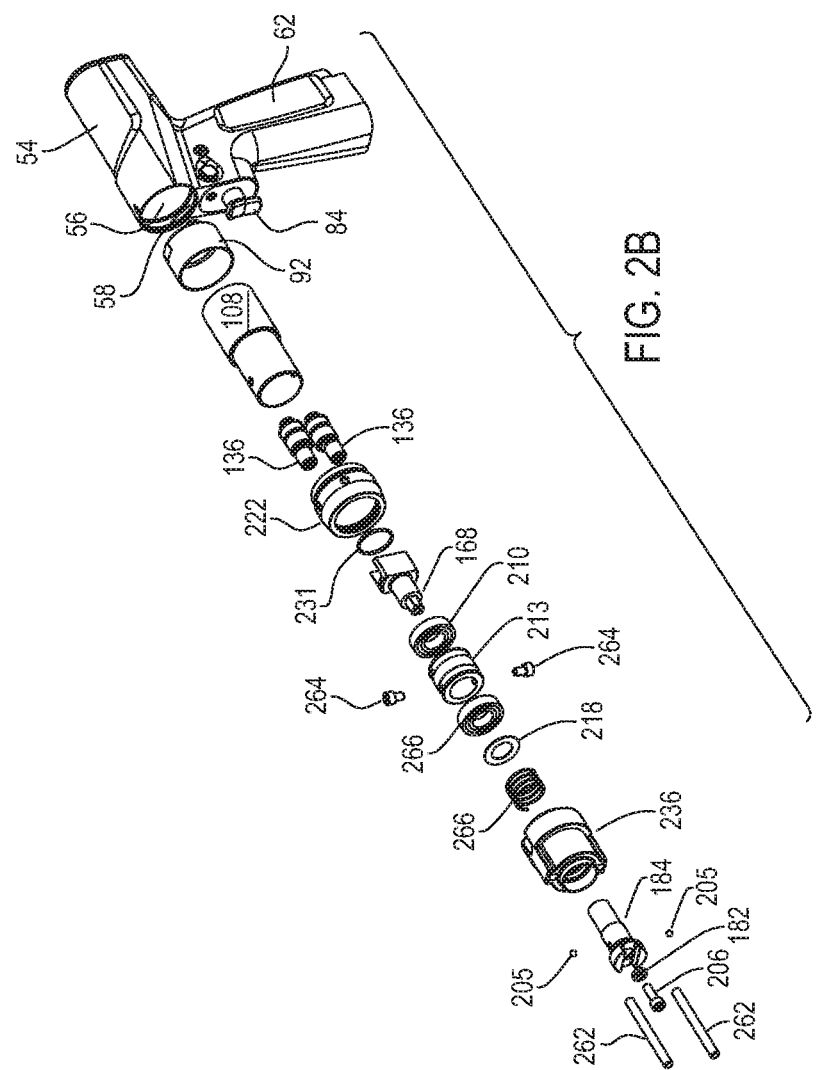

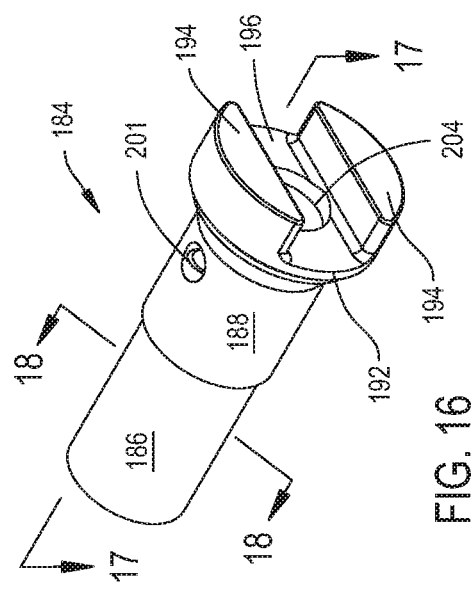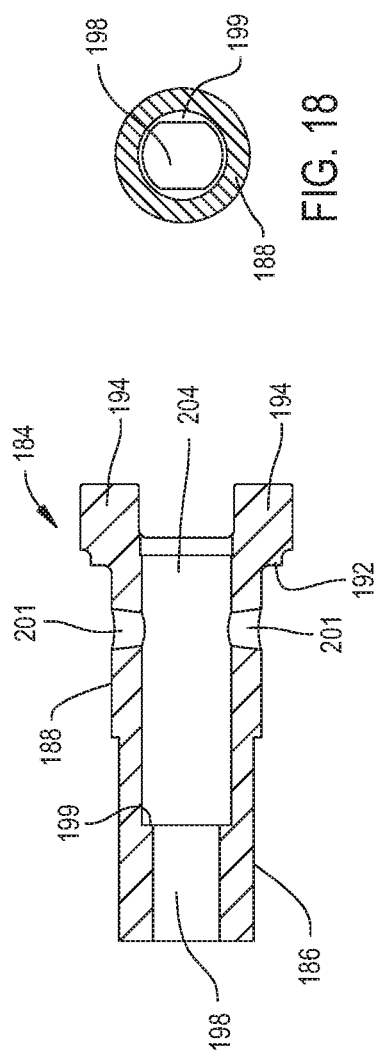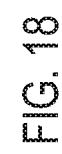

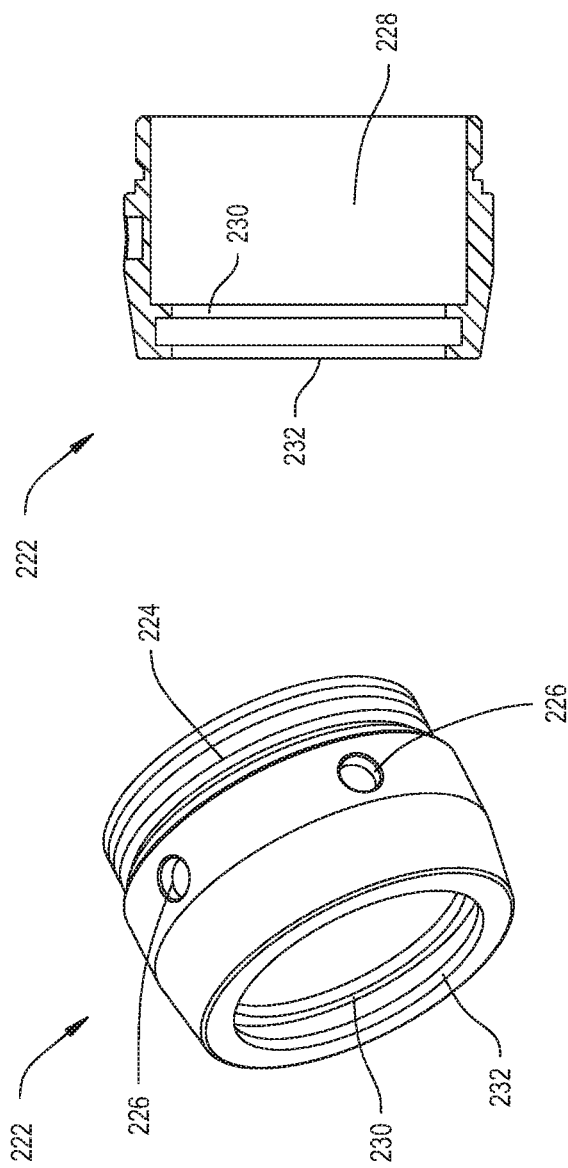

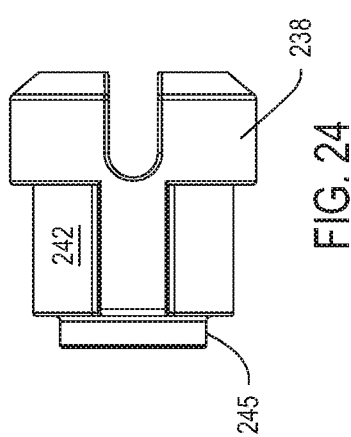
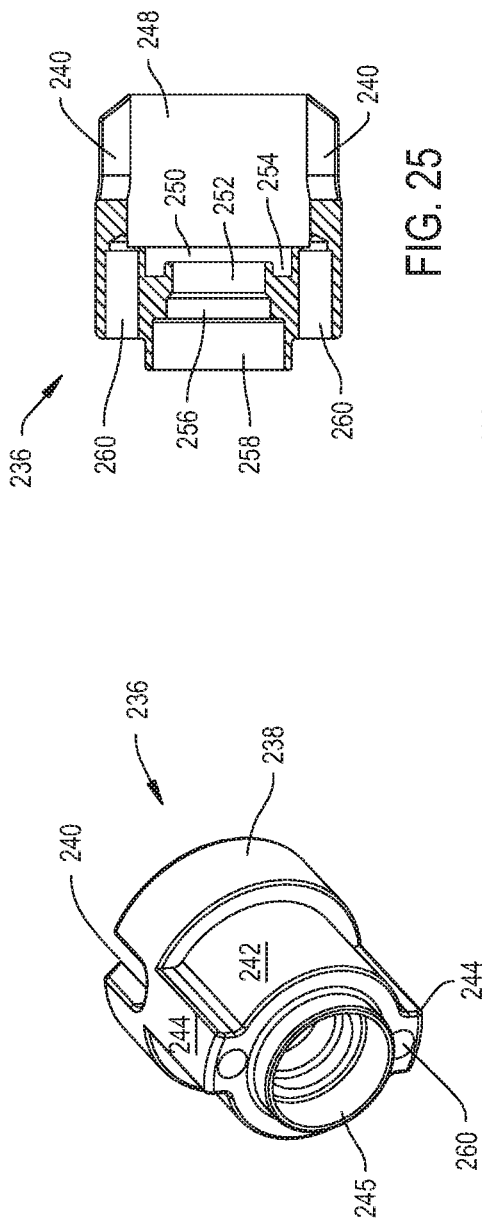

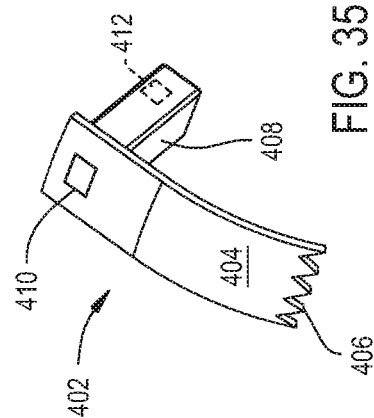
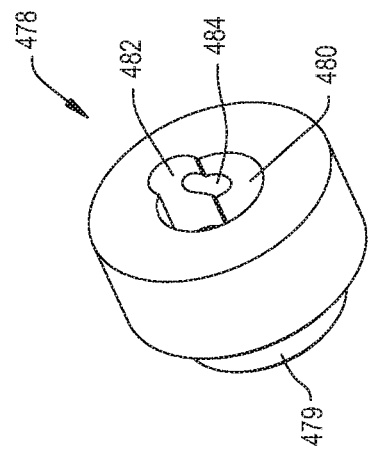
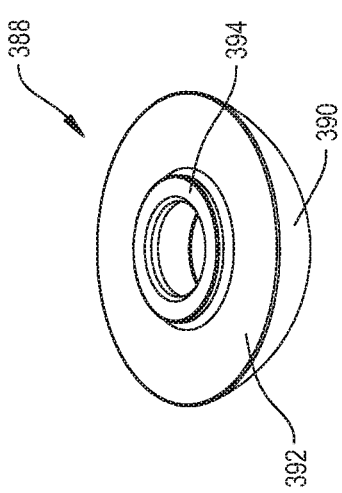
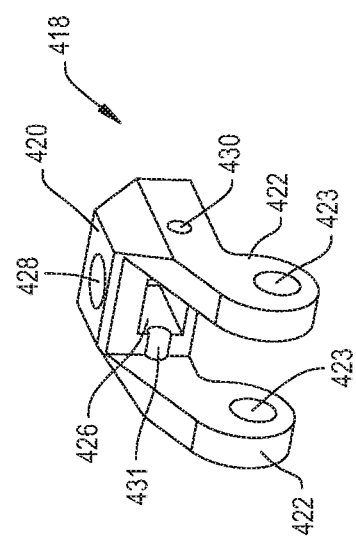

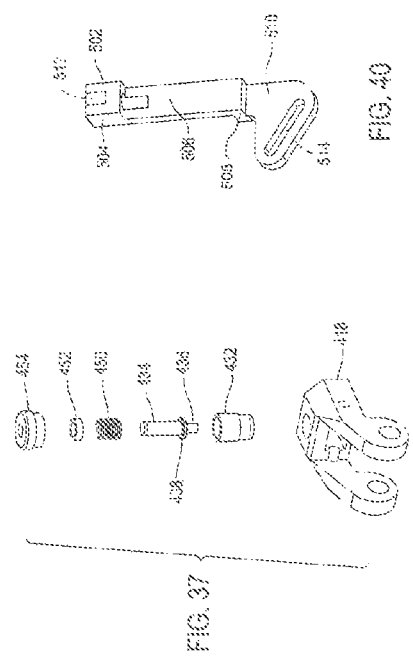

ACETABULAR CUP REMOVER WITH INDEXING ASSEMBLY FOR ROTATING THE REMOVAL BLADE AROUND THE CUP

RELATED APPLICATIONS

This application is a continuation of U.S. patent application Ser. No. 14/834,662, filed on Aug. 5, 2015, which is a continuation of PCT Pat. App. No. PCT/US2013/028535 filed on Mar. 1, 2013, now expired. The disclosures and contents of each priority application are hereby incorporated herein by reference in their entirety.

FIELD OF THE INVENTION

This invention relates generally to an acetabular cup remover. More particularly, the acetabular cup remover of this invention is able to rotate cup removable blade around the cup being removed.

BACKGROUND OF THE INVENTION

One area of the body which is highly prone to chronic pain and degeneration of normal function is the hip joint. Whether caused by disease, aging, overuse, or injury, a portion of the population suffers from ailments relating to the hip. An often-utilized solution to problems pertaining to the hip joint is total hip replacement ("THR") surgery. Generally, THR surgery consists of the replacement of the existing ball and socket of the hip joint with prosthetic replacements. The head of the femur (i.e.—the ball) is typically removed and replaced with a femoral component made of biocompatible material, which mirrors the structure of the original bone. The acetabulum (i.e.—the socket) is typically reamed and fitted with a prosthetic acetabular cup component that corresponds and cooperates with the femoral component. This prosthetic acetabular cup component often times includes an outer shell constructed of a metallic material. Typically, this shell is in the form of a hollowed out semi-sphere. An insert constructed of plastic, ceramic or metal received within the outer shell. In many cases, the acetabular cup component is anchored in the bone through the use of cement. Some cups are press fit in place. Still other cups are held in place by screws or fastening tabs integral with the cup itself. A combination of these fastening methods may be employed. Sometimes owing to the shape of the outer shell and/or the application of compound that enhance bone growth, the outer shell is designed to foster the growth of bone adjacent the shell. This new bone anchors the cup to the rest of the hip. Total hip replacement surgery has often proven successful in relieving many problems associated with the hip joint.

Even though total hip replacement surgery is often successful, it is sometimes necessary to perform the same surgery on the same hip. This may be necessary in situations in which wear or infection degrade the performance of the installed cup and femoral head. This sub-set of total hip replacement surgery is sometimes called revision surgery. In revision surgeries, it is necessary to remove the acetabular component previously implanted in the acetabulum. As mentioned above, these components may have been cemented in place or otherwise held by bone or fibrous tissue that may have grown in and around the component. Thus, their removal requires the cutting or chipping away of cement or bone material.

The Inventor's Assignee's U.S. Pat. No. 8,034,059, ACETABULAR SHELL REMOVAL INSTRUMENT, issued 11 Oct. 2011, the contents of which are explicitly incorporated herein by reference, discloses a surgical tool, acetabular cup remover, designed to perform a revision process. As its name implies, this tool is designed to remove an already implanted acetabular cup. This tool includes a head that is dimensioned to seat in and rotate in an implanted acetabular cup. Plural shafts extend away from this head. A blade is pivotally mounted to one of these shafts. The blade curves forward such that the blade curves around the head. One of the shafts is able to move longitudinally relative to the head. The blade is connected to this first shaft to pivot as a function of the longitudinal movement of the shaft. A second shaft is rigidly connected to the head. The blade is connected to this second shaft. Axial rotation of this second shaft results in a rotational movement of the blade around an arc. The second shaft is connected to a power tool that oscillates the shaft.

This tool is used by seating the head in the cup that is to be removed. The first shaft is pressed downwardly. This results in the pivoting of the blade against the bone in adjacent the cup. The power tool is actuated. Thus, simultaneously the blade is pressed against bone and oscillated in an arc around the cup. The blade cuts the bone adjacent the cup. The tool is indexed, and the blade pivoted so that the blade forms a cut that extend completely around the portion of the cup embedded in the bone. The formation of this cut separates the cup from the bone in which the cup is embedded. The cup can then be removed and a new one installed.

The above-described acetabular cup remover can be a useful tool for removing an acetabular cup. There is, however, an inefficiency associated with this tool. When the tool is used, the blade is typically oscillated around an arc that of 15° or less and more often 10° or less. Once one section of the cut is formed, the tool must be rotated so the blade can be positioned to cut an adjacent section of the cut. To form the cut it is necessary to rotate the power tool to which the cup remover is attached. This results in the centering of the blade over the portion of the bone in which the new section of the cut is to be formed. This requires the surgeon forming the cut to reposition how the power tool is held. Having to so reposition the tool may require the surgeon to hold the power tool in positions that, ergonomically, can impose a strain. Further, having to so reposition the handpiece can add to the time it takes to perform the revision surgical procedure. Having to perform these steps runs counter to one of the primary goals when performing surgery, that one should perform the procedure as quickly as possible to both minimize the likelihood the exposed tissue is open to infection and the amount of time the patient is held under anesthesia.

SUMMARY OF THE INVENTION

The present disclosure provides a method of indexing an acetabular cup remover. The method includes providing an acetabular cup remover assembly comprising a powered surgical driver and an acetabular cup remover coupled to the powered surgical driver. The acetabular cup remover comprises a shaft having a longitudinal axis that extends distally to proximally through the shaft, a blade disposed adjacent a distal end of the shaft that is shaped to extend around an acetabular cup. The blade is configured to pivot about a pivot axis that is transverse to the longitudinal axis. The method further includes positioning the acetabular cup remover against the acetabular cup with the blade in a first radial orientation relative to the longitudinal axis and the powered surgical driver. The method additionally includes displacing the blade to force the blade against a section of bone adjacent the acetabular cup of a patient. The method also includes actuating the powered surgical driver to oscillate the shaft to oscillate the blade to form a first arcuate cut into the bone. The method further includes rotating the blade about the longitudinal axis to a second radial orientation relative to the longitudinal axis and the powered surgical driver without disconnecting the shaft from the powered surgical driver. The method also includes actuating the powered surgical driver in the second rotational orientation to oscillate the shaft to oscillate the blade to form a second arcuate cut into the bone.

The present disclosure also provides another method of indexing an acetabular cup remover. The method includes providing an acetabular cup remover assembly comprising a powered surgical driver and an acetabular cup remover coupled to the powered surgical driver. The acetabular cup remover comprises a shaft having a longitudinal axis that extends distally to proximally through the shaft, a blade disposed adjacent a distal end of the shaft that is shaped to extend around an acetabular cup. The blade is configured to pivot about a pivot axis that is transverse to the longitudinal axis. The method further includes positioning the acetabular cup remover against the acetabular cup with the blade in a first radial orientation relative to the longitudinal axis and the powered surgical driver. The method additionally includes displacing the blade to force the blade against a section of bone adjacent the acetabular cup of a patient. The method also includes actuating the powered surgical driver to oscillate the shaft to oscillate the blade to form a first arcuate cut into the bone. The method further includes rotating the blade about the longitudinal axis to a second radial orientation relative to the longitudinal axis and the powered surgical driver while the shaft is connected to the powered surgical driver. The method also includes actuating the powered surgical driver in the second rotational orientation to oscillate the shaft to oscillate the blade to form a second arcuate cut into the bone.

BRIEF DESCRIPTION OF THE DRAWINGS

The invention is pointed out with particularity in the claims. The above and further features and benefits of this invention are understood by the following Detailed Description taken in conjunction with the accompanying drawings in which:

FIG. 2 is an assembly diagram depicted how FIGS. 2A and 2B are assembled together to form an exploded view of the components of this invention;

FIG. 16 is a perspective view of the output spindle of the driver;

FIG. 17 is a cross sectional view of the output spindle taken along line 17-17 of FIG. 16;

FIG. 18 is a cross sectional view of the output spindle taken along line 18-18 of FIG. 16;

FIG. 21 is a perspective view of the lock cap;

FIG. 22 is a cross sectional view of the lock cap;

FIG. 23 is a perspective view of the retainer associated with the driver;

FIG. 24 is a plan view of the retainer when viewed from the top;

FIG. 25 is a cross sectional view of the retainer;

FIG. 34 is a perspective view of the pivot head;

FIG. 35 is a perspective view of the blade;

FIG. 36 is a perspective view of the hinge;

FIG. 37 is an assembly view of the components attached to the hinge that releasably hold the blade to the hinge;

FIG. 39 depicts the lock collar disposed in the handle;

FIG. 40 depicts the actuator; and

DETAILED DESCRIPTION

I. Overview

Figure 1:
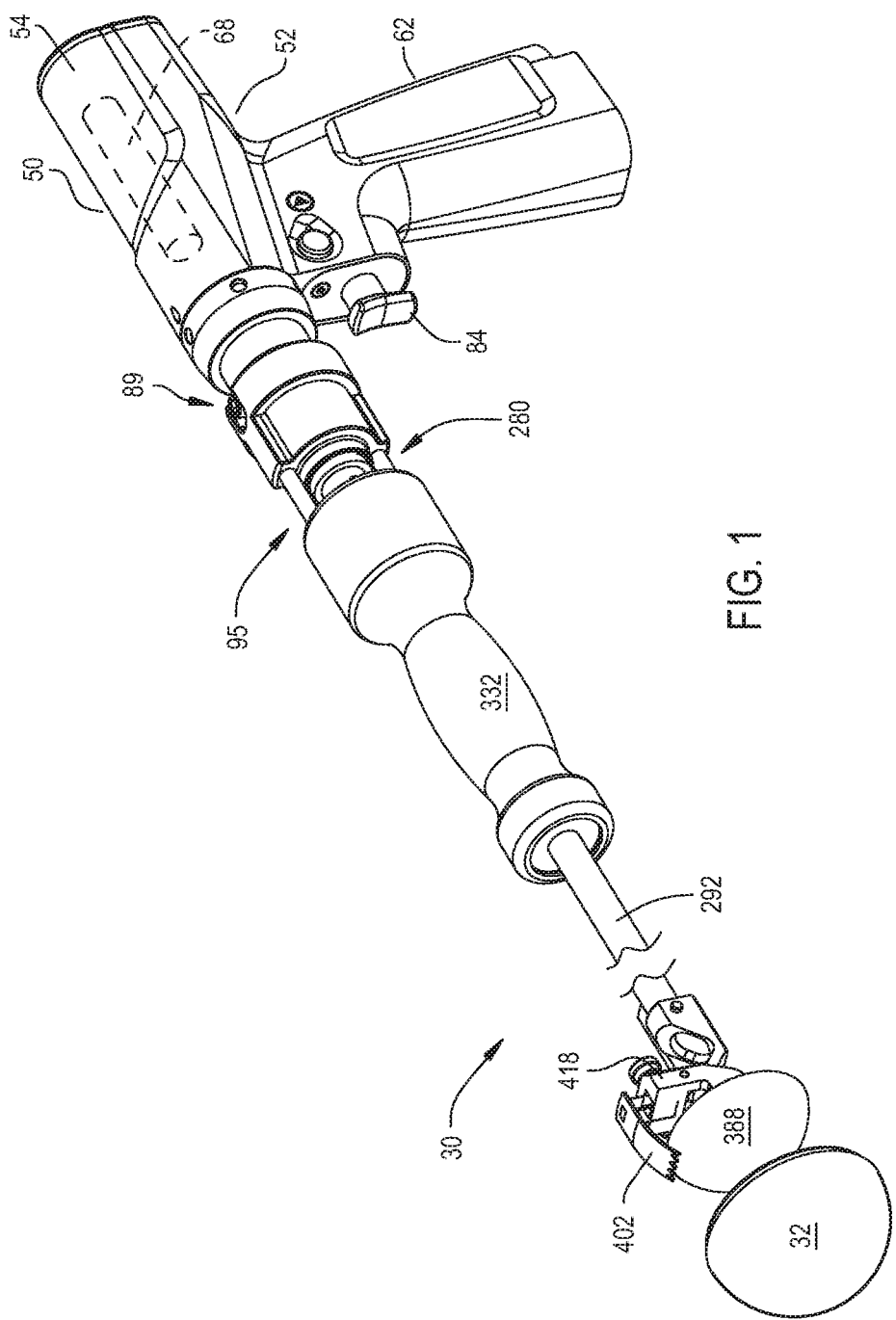
FIG. 1 is a perspective view of an acetabular cup remover of this invention.

FIG. 1 illustrates a surgical tool, acetabular cup remover 30, of this invention and the relation of the tool to an acetabular cup 32. The cup 32 is often in the form of a hollow semi-spherical structure typically formed of metal. The outer surface of the cup 32 is embedded in bone of the hip. The inner surface of the cup defines a socket. This socket was designed to receive the ball of a femoral stem. While not illustrated, a liner, often in the form of a hollow semi-spherical structure, may be seated against the inner surface of the cup 32. A liner, when present, defines the socket space that receives the femoral ball.

The cup remover 30 includes a pivot head 388. Head 388 is the portion of the cup remover 30 that is seated in the cup 32. A shaft 292 extends proximally from the head 388. ("Proximally," it is understood means towards the surgeon using the cup remover 30, away from the cup 32. "Distally" means away from the surgeon, towards the cup 32.) A blade 402 is pivotally attached to shaft 292 a short distance proximally rearward from the head. Blade 402 has an arcuate profile and is positioned so as to curve distally forward and around the head 388. More particularly, the blade 402 is shaped so that when the head 388 is seated in the cup 32 the blade, when pivoted distally forward, advances around the outer surface of the cup.

A hinge 418 is connected to shaft 292. Hinge 418 pivots the blade around a pivot axis so as to advance and retract the blade relative to the distal end of head 388. This pivot axis is understood to be in a static location relative to shaft 292. A handle 332 is slidably connected to the shaft 292. The handle 332 is connected to hinge 418 to pivot the hinge. Thus, the handle 332 and hinge 418 can collectively be considered a blade pivoting assembly.

Figure 4:
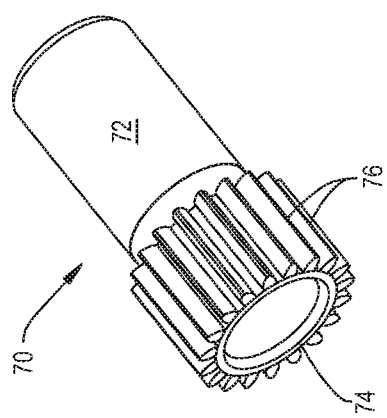
FIG. 4 is a perspective view of the motor shaft internal to the driver.

Cup remover 30 is actuated by a power tool, referred to as a driver 50. Driver 50 includes a motor 68. A coupling assembly 280 releasable connects the tool 30, namely the shaft 292 and handle 332, to driver 50. A transmission assembly 89 converts the rotational movement of a shaft 70 (FIG. 4) integral with the motor 68 into an oscillatory motion. This motion is transmitted by the coupling assembly to the cup remover shaft 292 as oscillatory motion. The oscillation of shaft 292 results in a like oscillation of the cup remover blade 402.

The driver transmission 89 and coupling assembly 280 also collectively form an indexing assembly 95. This indexing assembly allows the surgeon, by rotating handle 332, to set the rotational orientation of the cup remover shaft 292 around an axis that extends longitudinally through the shaft 292. The indexing of cup remover shaft 292 results in a like setting of the rotational orientation of blade 402 relative to cup 32.

II. Driver

Figure 3:
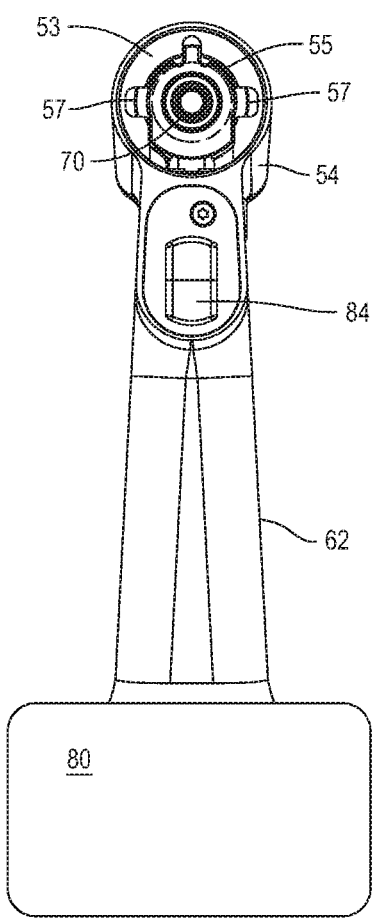
FIG. 3 is a plan view looking into the distal end of the driver.

One powered driver 50 that can be employed with cup remover 30 is now described with respect to FIGS. 1, 2B and 3. Driver 50 includes a housing 52. In the particular version of the invention, housing 52 is shaped to have a barrel 54 that forms the head of the housing. The housing 52 is further formed so as to have a bore 56 that extends inwardly from the distally directed face of barrel 54. The cylindrical inner wall of housing 52 that defines bore 56 is formed with threading 58. The threading 58 is locating in the section of the wall immediately proximal to the distal open end of bore 56. Internal to housing is a web 53. Web 53 defines the proximal end of bore 56. The web 53 is formed with a center opening 55 and a pair of notches 57 located on the opposed sides of the opening. A pistol-grip shaped handle 62, also part of the housing 52, extends downwardly from head 54.

Figure 5:
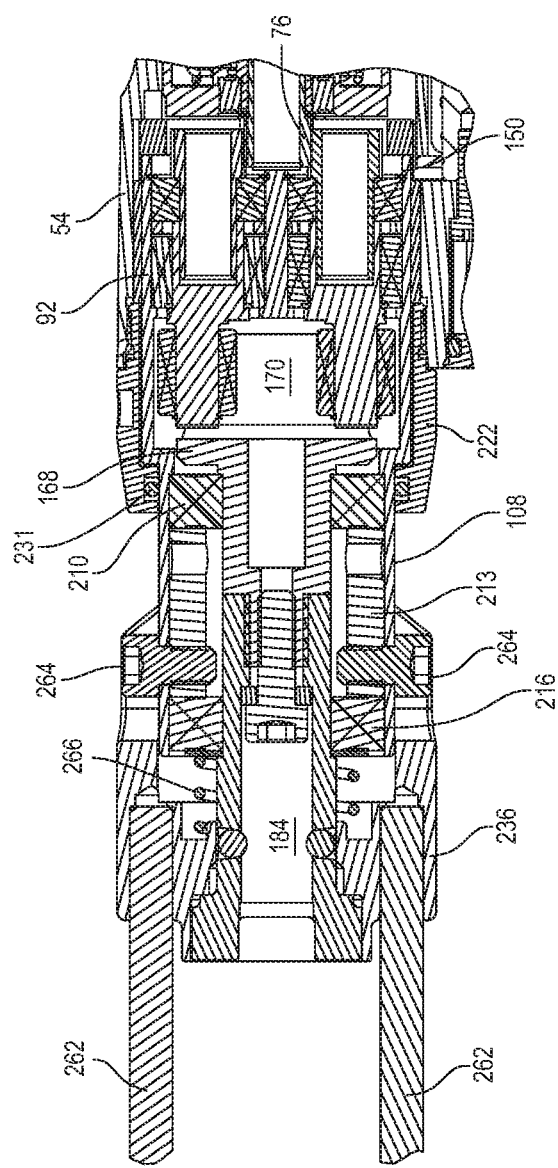
FIG. 5 is a cross sectional view of the transmission components and coupling components attached to the driver.

A motor 68, represented by a phantom cylinder, is disposed inside housing barrel 54. In some versions of the invention, the motor 68 is a brushless DC motor. It should be appreciated that this is exemplary, not limiting. In other versions of the invention, the motor may be a DC motor with brushes, an AC driven motor or a motor that is pneumatically or hydraulically driven. Motor 68 includes a rotating shaft 70. As seen in FIG. 5 motor shaft 70 includes a cylindrical stem 72. In versions of the invention in which the motor 68 is an electric motor, the stem 72 is the portion of the motor disposed in the motor stator. A head 74 forms the distalmost section of the shaft 70. The head 74 is cylindrical and coaxial with the stem 72. The head 74 is formed to have gear teeth 76. Driver 50 is assembled so that the casing of the motor (casing not identified seats in web opening 55. As a consequence of this positioning of the motor 68, the shaft head 74 is disposed in the proximal end of driver housing bore 56. Not described and not part of this invention are the structural components of the driver 50 that protect the components of the motor 68 not disposed in bore 56 from the adverse effects of autoclave sterilization.

In the illustrated version of the invention, driver 50 is a cordless tool. A battery 80, seen only in FIG. 3, is removably attached to the butt end of the handle 62 contains a charge for energizing the motor. Again, it should be understood that the invention is not so limited. In alternative versions of the invention, a power cord, an air line or a fluid line may be connected to the handpiece for providing the power needed to actuate the motor.

A trigger 84 is moveably mounted to the driver housing 52. In the illustrated version of the invention, trigger 84 extends distally forward from the handle 66 immediately below the barrel 54. A control circuit internal to the handle 66, not illustrated and not part of this invention, monitors the actuation of the trigger 84. Based on the extent to which the trigger switch 84 is actuated, the control circuit selectively energizes the motor 68 to cause an shaft 70 to rotate at the desired speed.

Figure 7:
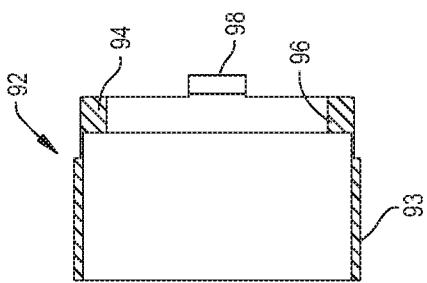
FIG. 7 is a cross sectional view of the cup insert.
Figure 6:
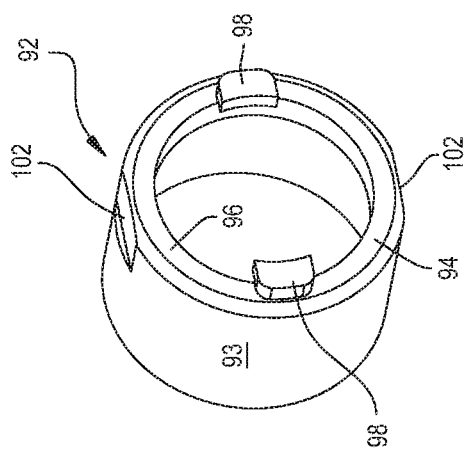
FIG. 6 is a perspective view of the cup insert fitted to the driver.

As seen by FIGS. 2B and 5, a number of components of the transmission assembly 89 are mounted in the driver housing bore 56. One of these components is a generally cylindrical cup insert 92 now described by reference to FIGS. 6 and 7. The cup insert 90 is formed from a single piece of material typically hardened steel. Cup insert 92 is shaped to have generally tube-shaped main body 93. The outer diameter of the main body 93 is dimensioned to closely slip fit in drive housing bore 56. A ring-shaped base 94 extends proximally from body 93. Base 97 has inner and outer diameters slightly less than those of body 93. Two feet 98 project proximally away from the proximal end of base 94. Feet 98 are diametrically opposed to each other around the longitudinal axis that extends through the cup insert. Feet 98 are dimensioned to, when the driver 50 is assembly closely seat in driver notches 57.

Cup insert 92 is further formed to have adjacent the proximal end two flats 102. Flats 102 extend distally from the proximal end of the main body 93. Each flat 102 is, relative to the longitudinal axis of the cup insert 90, spaced from the adjacent teeth 98. Flats 102 are not part of the present invention.

Figure 10:
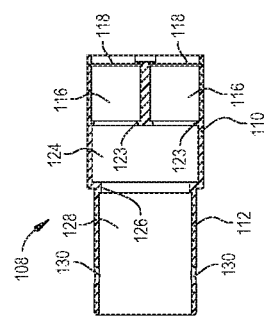
FIG. 10 is a cross sectional view of the eccentric housing taken along line 10-10 of FIG. 9.
Figure 9:
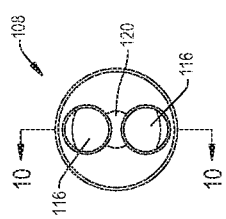
FIG. 9 is a plan view of the proximal end of the eccentric housing.
Figure 8:
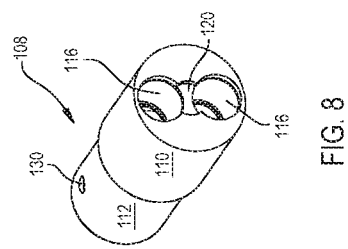
FIG. 8 is a perspective view of the eccentric housing.

An eccentric housing 108, seen best in FIGS. 8-10, is rotatably seated in cup insert 92. Eccentric housing is formed is a single piece component typically formed from hardened steel. Eccentric housing 108 is formed to have a base 110 and a stem 112, both of which are cylindrical in shape. The base 110 has an outer diameter greater than that of stem 112. Base 110 has a diameter that allows the base to closely slip fit and rotate in the void space with the cup insert main body 93. The proximal end of the base is solid. Two parallel bores 116 extends longitudinally through the solid portion of the base 110. Bores 116 extend from the proximal end of the base 110. The bores 116 are diametrically opposed to each other relative to the longitudinal axis through the eccentric housing 108. The eccentric housing 108 is further formed so an annular groove 118 extends outwardly from each of the interior cylindrical walls of the housing that define a separate one of the bores 116. Each groove 118 protrudes outwardly from the bore 116 at a location that is slightly forward from the proximal ends of the bores.

The eccentric housing 108 is further formed so that there a recess 120 extends inwardly from the proximal face of the housing. Recess 120 defines a circle that is centered on the longitudinal axis through the housing 108. Recess has an outer diameter that allows the head 74 of the motor shaft 70 to seat in the recess. It should thus be appreciated that the recess 120 intersects the open proximal ends of bores 116.

The proximal ends of bores 116 open into a common bore 124. Bore 124 is formed in the distal portion of the eccentric base 110. Bore 124 is cylindrical in shape and coaxial with the longitudinal axis through the eccentric housing 108. The proximal end of bore 124 opens into a coaxial cylindrical bore 128. Bore 128 is formed in the housing stem 112. Bore 128 extends to the distal end of the eccentric housing 108. Eccentric housing 108 is further formed to have an interior located ring-shaped ledge 126. Ledge 126 is located at the step between the housing base 110 and stem 112. Ledge thus defines a small disc like space (not identified) within the housing 108 between bore 124 and bore 128.

Eccentric housing 108 is further formed to have two diametrically opposed openings 130. Each opening 130 extends laterally through the housing stem 112 into bore 128.

Figure 11:
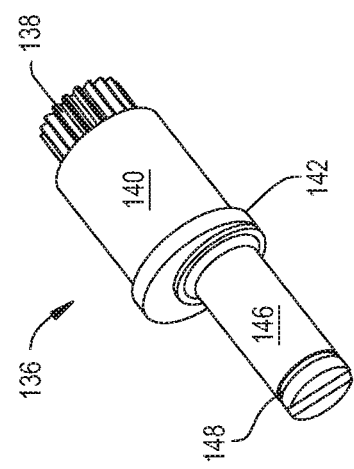
FIG. 11 is a perspective view of an eccentric shaft.

An eccentric shaft 136, seen in FIG. 11, is rotatably disposed in each bore 116 of the eccentric housing 108. Each eccentric shaft includes a cylindrical foot 138. The foot 138 is formed with teeth (not identified) dimensioned to engage the teeth 76 of motor shaft 70. A cylindrical leg 140 extends distally from the foot 138. Leg 140 extends to a ring-shaped collar 142. Collar 142 is coaxial with foot 138 and leg 140 and has a greater outer diameter than the leg 140. A cylindrical head 146 extends distally forward from collar 142. The longitudinal axis of head 146 is parallel with and laterally offset from the common longitudinal axis through shaft foot 138, leg 140 and collar 142. Immediately proximal to the distal end of the head 146, the eccentric shaft 136 is formed to have an annular groove 148 that extends circumferentially around the outer surface of the head.

In some versions of the invention, for ease of manufacture, foot 138 is formed as a separate component. A stem (not identified) extends upwardly from the foot. The shaft leg is formed with a bore (not identified) that is that extends distally from the proximal end of the leg. The stem integral with the foot 138 is press fit into the bore internal to the leg 140.

Figure 13:
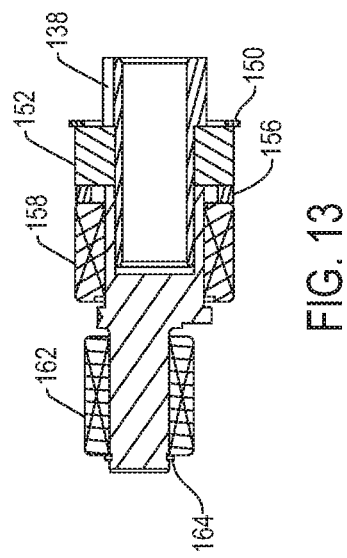
FIG. 13 is a cross sectional view of the sub assembly of FIG. 12.
Figure 12:
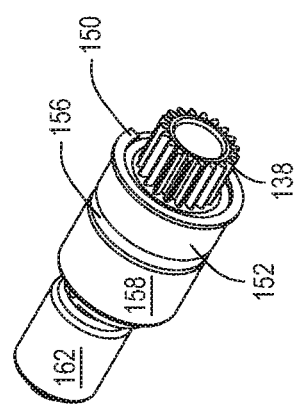
FIG. 12 is a perspective view of the eccentric shaft and bearing assemblies fitted over the shaft.

Two bearing assemblies 152 and 158, seen best in FIGS. 12 and 13, rotatably hold each eccentric shaft 136 in the eccentric housing bore 116 in which the shaft is seated. While not depicted, it should be understood that each bearing assembly includes inner and outer races and a set of ball bearings between the races. The inner races of the bearing assemblies 152 and 158 are dimensioned to press fit over the adjacent shaft leg 140. The outer races of the bearing assemblies 152 and 158 are dimensioned to tightly fit in the bore 116 in which the assemblies are seated. Bearing assembly 152 is the proximal of the two bearing assemblies. Bearing assembly 152 is positioned on shaft 136 so that the inner race of the assembly is located immediately forward of the proximal end of shaft leg 140. A snap ring 150, the purpose of which is discussed below, is sandwiched between the foot 138 and the proximal end of the leg 140.

Bearing assembly 158 is located forward of bearing assembly 152. In the illustrated version of the invention, bearing assembly 158 is longer in length than bearing assembly 152. The inner race of bearing assembly 158 is seated against the proximally facing surface of shaft collar 142 that extends radially outwardly of shaft leg 140.

Each eccentric shaft 136 and associated bearing assemblies 152 and 158 are seated in the eccentric housing 108 so that the outer races of bearing assemblies seat against the inner cylindrical wall of the housing that defines a bore 116. Snap ring 150 is disposed in the groove 118 contiguous with the bore 116. The proximally directed face of the outer race of bearing assembly 152 seats against the adjacent exposed face of the snap ring 150. The snap ring 150 thus holds the shaft and bearing assemblies 152 and 158 in the bore 116. A spacer 156 is disposed between the adjacent linearly aligned bearing assemblies 152 and 158. Spacer 156 is a ring formed from metal or plastic. The components of this invention are selected such that the outer surface of the spacer 156 is disposed against the adjacent bore 116 defining wall. Forward movement of the shaft 136 and bearing assemblies 152 and 158 is blocked by the abutment of the distally directed surface of the outer race of bearing assembly 158 against the adjacent proximally directed face of the ledge 123 internal to the eccentric housing.

Upon the mounting of the eccentric shafts 136 to the eccentric housing 108, the shaft feet 136 extend partially out the proximal end of the housing. The shaft heads 146 are disposed in the bore 124 internal to the housing 108. A bearing assembly 162 is disposed over each shaft head 146. Bearing assemblies 162 each include an inner and outer race (not illustrated. The inner race is tightly fit of the shaft head 144. A snap ring 164 disposed in groove 148 that extends inwardly from shaft head 148. The snap ring 164 extends over the inner race of the adjacent bearing assembly 162 so as to hold the bearing assembly to the shaft head 146.

When driver 50 is assembled, the eccentric housing 108 with components disposed therein is seated in the cup insert 92. More particularly, the proximal portion of the eccentric housing base 110 is disposed against the inner cylindrical wall of the cup insert main body 93. The proximal end of eccentric housing 108 is disposed against the distally directed face of cup inset base 94. The toothed feet 138 of the eccentric shafts 136 are located adjacent and engage the teeth 76 integral with the drive motor shaft. There is a close slip fit between the cup insert 92 and the eccentric housing. Owing to the dimensioning of these components and the material from which they are formed, the eccentric housing 108 is able to rotate within the cup insert 92. By extension, the eccentric housing 108 is able to rotate around the extension of an axial line that extends out of the drive housing barrel 54.

Figure 15:
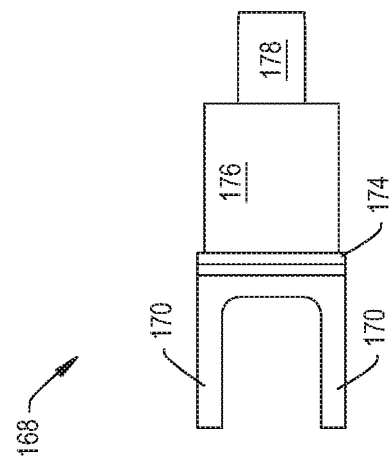
FIG. 15 is a plan view of the link.
Figure 14:
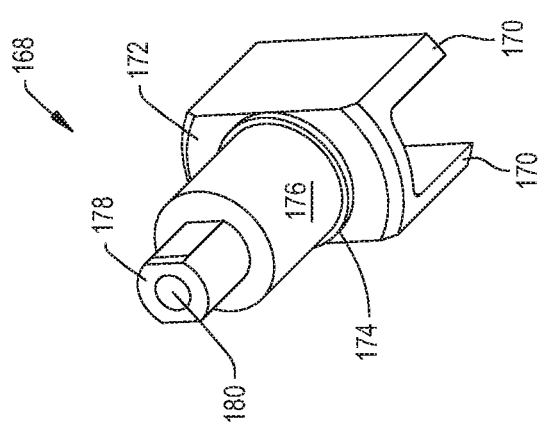
FIG. 14 is a perspective view of the link.

A link 168, now described by reference to FIGS. 14 and 15, is also disposed in eccentric housing 108. Link 168 is a single piece component formed from hardened steel. The link 168 is shaped to have two planar, rectangularly shaped plates 170. Plates 170 are parallel and spaced apart so that the plates can closely fit over bearing assemblies 162. The plates 170 extend distally forward to a common web 172. Web 172 is planar in shape and has a perimeter that is generally oval. A cylindrical head 176 extends distally forward from face of web 172 opposite the face from which plates 170 extend. The head 176 extends outwardly from the center of web 172. Immediately adjacent the web 172 a collar 174 extends around the proximal end of head 176. The collar 174 projects radially outwardly beyond the outer surface of head 176.

Link 168 is further formed to have a nose 178 that extends from the distal end of the head 176. Nose 178 is stepped inwardly from the outer perimeter of head 176. The nose is shaped to have two flat outer surfaces (not identified). These surfaces are parallel to each other and to plates 170. A curved surface (not identified) extends between each pair of opposed ends of the ends of the flat surfaces. A bore 180 extends proximally inward from the distal end of nose 178. The internal wall internal to the link nose 176 that defines bore 180 is formed with threading (not illustrated). Nose 178 and bore 180 are coaxial with link head 176.

An output spindle 184, now described by reference to FIGS. 16-18, extends forward from link 168. The output spindle 184 is formed as a single component and formed out of metal such as hardened steel. The output spindle 168 is formed to have cylindrical foot 186. Foot 186 has an outer diameter equal to the diameter of link head 176. A cylindrical leg 188 is coaxial with foot 186 and extends distally forward of the foot. Leg 188 has an outer diameter greater than that of the foot 186. Forward of leg 188, the output spindle 184 has a circular head 190. Head 192 extends radially outwardly from leg 188. Head 190 is coaxial with foot 186 and leg 188. Two ears 194 project forward from head 190. Each ear 194 is in the form of a slice section of the circle subtended by head. The ears 194 are spaced apart from each other so as to define an annular notch 196 therebetween. Notch 196 extends diametrically across the output spindle. The distally directed face of the head 192 forms the base of notch 196.

Output spindle 184 is further shaped so as to have a bore 198 that extends forward from the proximal end of the spindle foot 186. Bore 198, as seen in FIG. 18, has what is referred to as a double-D shape. More particularly, the bore 198 is shaped to closely receive link nose 178. Bore 198 extends approximately one-half way through spindle foot 186. Bore 198 opens into a cylindrical bore 204. Bore 204 is coaxial with bore 198 and extends through the distal portion of foot 186, leg 188, neck 190 and head 192. A step 199, is the transition surface internal to the spindle foot 186 between bore 202 and bore 204. Bore 204 opens into the exposed face of the head 190, the surface of the head that defines the base of notch 196.

Spindle leg 188 is formed to have two diametrically opposed openings 201. Openings 201 open into bore 204. Each opening 201 is the form is tapered such that the narrow diameter portion of the opening forms the inlet into the bore 204. A ball bearing 205 is seated in each opening 201. When the ball bearing 205 is fully seated in the associated opening 201, a portion of the bearing protrudes into spindle bore 204.

The foot 188 of output spindle 184 is seated over the nose 178 integral with link 168, as seen in FIGS. 2B and 5. The link nose 178 extends into bore 198 internal to the output spindle 184. A washer 182, identified only in FIG. 2B, is seated over the step 199 internal to the output spindle 184. A threaded fastener 206, identified only in FIG. 2B, is seated in the spindle bores 198 and 204. Fastener 206 is threaded into bore 180 internal link 168. The head of fastener 206 seats against washer 182.

Bearing assemblies 210 and 216 rotatably hold link 168 and output spindle 184 in eccentric housing bore 128. While not seen, it is understood both bearing assemblies 210 and 216 include inner and outer races. The outer races of both bearing assemblies 210 and 216 are disposed against the surface internal to the eccentric housing stem 112 that defines bore 128. The inner race of the proximalmost bearing assembly, assembly 210, is seated over link head 176. The proximal end of the inner race of bearing assembly 210 is disposed against the distally directed face of the link collar 174.

Figure 20:
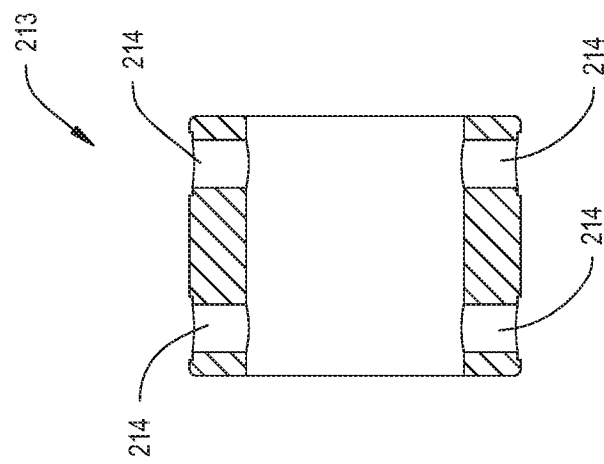
FIG. 20 is a cross sectional view of the spacer of FIG. 19.
Figure 19:
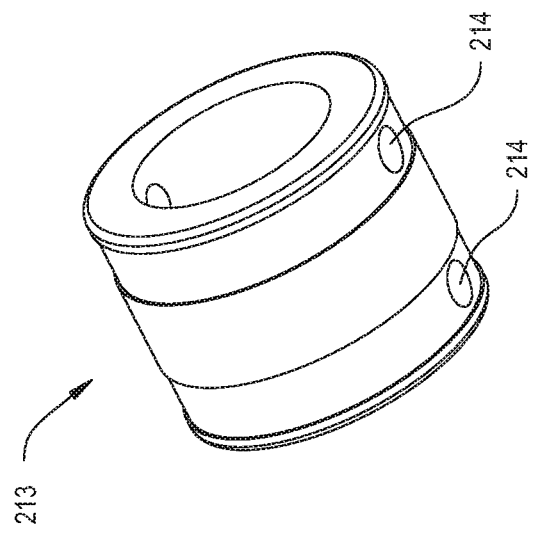
FIG. 19 is a perspective view of a spacer internal to the eccentric housing.

A spacer 213 disposed within eccentric housing bore 128 holds bearing assembly 216 distally away from bearing assembly 210. Spacer 213 is formed from aluminum and is tube shaped, as seen in FIGS. 19 and 20. Spacer 213 has an outer diameter that facilitates the non-rotational fitting of the spacer against the inner cylindrical wall of housing stem 112. The inner diameter of the spacer 213 is such that there is a clearance between the spacer and the link head 176 and output spindle foot 186 that are disposed within the spacer. The spacer is formed with two pairs of diametrically opposed threaded openings 214. The pairs of the openings are symmetric relative to a lateral plane that bisects the spacer. Each opening 214 open into the center void of the spacer 213. As will be apparent below this invention requires only a single pair of openings 214. The second pair of openings is provided for ease of assembly.

When the driver 50 is assembled, the proximally directed face of spacer 213 rests against the adjacent face of the outer race of bearing assembly 210. The proximally directed of the outer race of bearing assembly 216 seats against the adjacent distally directed face of spacer 213. The inner race of bearing assembly 216 is disposed around the foot 186 of the output spindle 184. The distal end of the inner race of bearing assembly 216 is located adjacent the step that defines the transition between spindle foot 186 and leg 188, step not identified. In the depicted version of the invention, a washer 218, identified only in FIG. 2B, is sandwiched between the bearing assembly 216 and the step. Upon assembly of the driver, leg 188, head 190 and ears 194 of the output spindle 184 are located forward of the eccentric housing 108.

A lock cap 222, best seen in FIGS. 21 and 22 holds the eccentric housing 108 and the components disposed therein to the driver 50. The lock cap 222 is generally in the form of a tube. The proximal end of the tube portion of the lock cap is provided with threading 224 around the outer surface, threading seen only in FIG. 21. More specifically, this portion of the lock cap 222 is designed to seat in housing bore 56 so the cap threading 224 can engage the driver housing threading 58. The distal portion of the lock cap is formed to have an outer surface that extending distally along the cap, tapers inwardly. Proximal to the inwardly tapered surface, the cap 222 is formed to have a number of closed end bores 226. Bores 226 are provided to receive a tool (not illustrated) able to rotate the cap 168.

Owing to the tube-like shape, the inside of the lock cap 222 is a void space 228. The cap is further formed to have two annular lips 230 and 232 that extend inwardly from the inner wall of the cap into this void space. The proximalmost of these lips, lip 230, is located less than 0.5 cm from the distal end of the cap. The distalmost lip, lip 232, extends inwardly from the distal end of the cap 222. Relative to the longitudinal axis through the lock cap 222, lips 230 and 232 are spaced apart from each other.

When the driver 50 is assembled, the eccentric housing 108 and components seated in the housing are fitted in drive housing bore 56. Lock cap 222 is screw secured in bore 56. The proximal movement of the lock cap 222 into the housing barrel 54 is limited by the abutment of the proximal end of the cap against the adjacent distal end of the cup insert 92. The components of this invention are dimensioned so the outer surface of the eccentric housing base 108 is spaced inwardly from the surrounding inner surface of the lock cap 222. Lock cap lip 230 extends over the stepped surface of the eccentric housing that separates the base 110 from the stem 112. This arrangement holds the eccentric housing 108 for rotation to driver housing barrel 54. Eccentric housing stem 112 extends forward of the lock cap 222.

As part of the assembly process an O-ring 231 is seated between lock cap lips 230 and 232. The O-ring 231, identified in FIGS. 2B and 5, provides a seal between the eccentric housing 108 and the lock cap 222.

A retainer 236, initially described by reference to FIGS. 23-25, is disposed over both the distal portion of the eccentric housing 108 and the portion of the output spindle 184 that extends forward of the housing. The retainer 236 is formed as a single piece unit and has a ring-shaped skirt 238 that forms the proximal portion of the retainer. Two diametrically opposed slots 240 extend forward from the proximal end of the skirt 238. In the depicted version of the invention, the slots 240 are U-shaped. A tube-shaped collar 242 is integral with and extends distally forward from skirt 238. Collar 242 has an outer diameter less than that of skirt 238. Two diametrically opposed ribs 244 project outwardly from the distal end of collar 242. Each rib 244 is longitudinally aligned with a separate one of the slots 240 Each rib 244 extends proximally so as to terminate at the step between the skirt 238 and collar 240, (step not identified). A ring like neck 245 extends distally forward from collar 240. Neck 245 has an outer diameter less than that of the adjacent collar 242.

Retainer 236 is formed to have a number of void spaces. One of these void spaces is a bore 248. Bore 248 extends forward from the proximal end of the skirt 238. The bore 248 extends longitudinally through the whole of the skirt 238 and an adjacent proximal portion of collar 240. The retainer 236 is dimensioned so that bore 248 can receive in sliding engagement stem 112 of eccentric housing 108. Slots 240 open into bore 236. Four bores, all coaxial with bore 248, extend distally from bore 236 to the distal end of retainer neck 242. Bore 250 is the bore immediately distal to and contiguous with bore 248. Bore 250 has a diameter less than that of bore 248. Bore 250 opens into a bore 252. Bore 252 has a diameter less than that of bore 250. Bore 252 also opens into an annular groove 254 also disposed within retainer collar 240. Groove 254 is radially spaced from and extends around the proximal portion of bore 252. The outer diameter of groove 252 is equal to the diameter of bore 250.

Bore 256 is the bore that is immediately distal to and contiguous with bore 252. Bore 256 has a diameter greater than that of bore 252. Like bore 252, bore 256 is disposed wholly within retainer collar 240. Bore 256 opens into bore 258, the distalmost of the retainer bores. Bore 258 has a diameter greater than that of bore 256. More particularly bore 258 has a diameter that allows the slip fitting of the output spindle head 192 and ears 194 in the bore 258. Bore 258 extends through the distal end of the retainer collar 240 and through the whole of retainer neck 242.

Retainer 236 is formed to have two additional bores, bores 260. Each bore 260 is a closed end bore formed in one of the ribs 230. Each bore 260 extends from the distally directed face of the rib 230 in which the bore is located. Bores 260 are parallel to the proximal-to-distal longitudinal axis through the retainer 222. A cylindrical pin 262, seen in FIGS. 2B and 5, is press fit in each bore 260. Pins 262 extend forward from retainer 236.

When driver 50 is assembled, two screws 264, seen in FIGS. 2B and 5, are fitted to the eccentric housing 108. Each screw 264 is seated in one of the openings 130 in the housing stem 112. The shaft of each screw is threaded into the spacer opening 214 in registration with the eccentric housing opening 130. Retainer 236 is slip fitted over the eccentric housing stem 112 so that the head of each screw 264 seats in a separate one of the retainer slots 240. A coil spring 266 is placed in front of bearing assembly 216. The output spindle 184 is secured to link 168 with fastener 206.

As a consequence of the mating of the output spindle 184 to the rest of the driver 50, the spindle neck 192 and head 194 seat, respectively, in retainer bore 256 and bore 258. The distal end of the spring 266 seats in the annular surface internal to the retainer 236 that defines groove 254. Spring 266 exerts a force on the retainer 236 that pushes the retainer distally away from the eccentric housing 108. The distal movement of the retainer 236 is limited by the abutment of the annular walls internal to the retain that define the transition from bore 256 to bore 258 to the adjacent faces of the output spindle that define the transition from the spindle neck 192 to the spindle head 194. When the retainer 236 is so positioned, the section of the spindle leg 188 that defines the openings 201 is surrounded by the ring like internal section of the retainer 236 that separates bore 252 from groove 254. This section of the retainer 236 thus blocks the outward movement of the ball bearings 205 out of spindle openings 201. It should further be appreciated that, upon assembly of the driver 50, pins 262 extend forward of the output spindle 184 and form the distalmost components of the driver 50.

The components of the driver 50 internal to the eccentric housing 108 form the transmission components that convert the rotary motion of driver shaft 70 into an oscillatory motion. The output spindle 184, bearings 205, retainer 236 and spring 266 form the driver portion of the coupling assembly 280 that removably hold the cup remover 30 to the driver 50. As discussed below these components also form part of the blade indexing assembly 95.

III. Cup Remover

Figure 26:
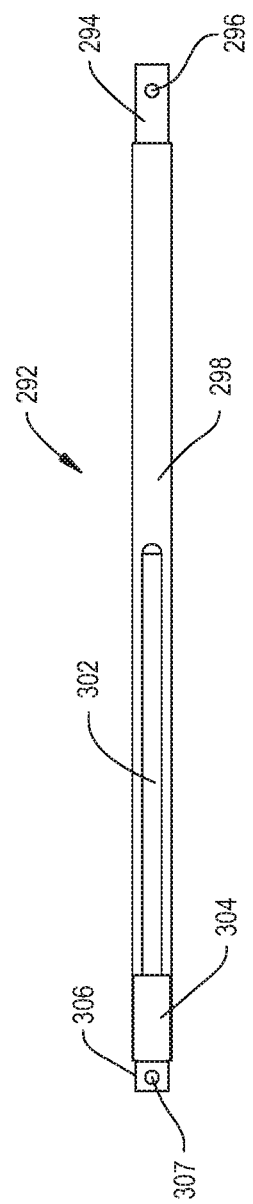
FIG. 26 is plan view of the shaft of the cup remover.

Shaft 292, now described with reference to FIG. 26 is one of the components of the cup remover 30 that transfers the rotational and oscillatory movement of driver link 168 to the blade 402. Shaft 292 is generally in the form of an elongated rod. At the proximal end, shaft 292 has a cylindrical stem 294. A bore 296 extends laterally through the stem 294. Proximal to stem 294, the shaft 292 has a trunk 298. Trunk 298 is generally cylindrical in shape and has a diameter greater than that of the stem 294. Trunk 298 is further formed to a longitudinally extending groove 302. Groove 302 extends distally forward from a location approximately one-half way along the length of the trunk. Groove 302 is concave in shape. The groove 302 extends forward to and opens above a flat 304 formed in the trunk 298. Generally speaking, the shaft 292 is formed so that the curved section of the trunk that defines the flat 304 subtends an angle of at least 180° around the longitudinal axis of the shaft.

Forward of trunk 298, the shaft 292 has a cylindrical head 306. Head 306 is coaxial with the stem 294 and trunk 298. The head 306 thus has a section that extends above flat 304. In the depicted version of the invention, head 306 has a smaller diameter then the diameter of the trunk 298. A bore 307 extends laterally through the head 304.

Figure 27:
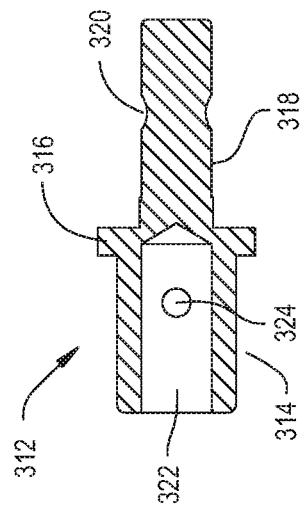
FIG. 27 is a perspective view of the input spindle of the cup remover.
Figure 28:
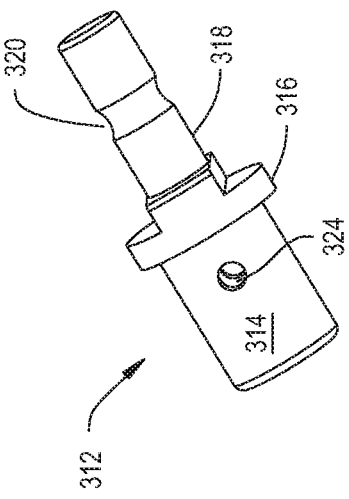
FIG. 28 is a cross sectional view of the input spindle.

An input spindle 312, seen best in FIGS. 27 and 28, releasably connects shaft 292 to the driver 50. Spindle 312 includes a cylindrical base 314. A circular collar 316 extends proximally from base 314. Collar 316 has an outer diameter that is greater than that of base 314. More specifically, the outer diameter of collar 316 is equal to the diameter of the circle defined by ears 194 integral with the output spindle 184 integral with driver 50. A neck 318 projects outwardly from the exposed face of collar 316. The neck 318 is in the form of a bar that extends diametrically across the face of collar 316. The minor surfaces of the bar forming neck are curved so as to be flush with the outer perimeter of the collar 316. The side-to-side width across the neck 318 is such that the neck can be close slip fitted in notch 196 formed by the output spindle 184.

Input spindle 312 is further formed so that a generally cylindrical head 318 extends proximally away from neck 318. Head 318 is coaxial with base 314 and collar 316. The head 318 has a diameter that allows the head to be closely slip fitted into bore 204 internal to the output spindle 184. The input spindle 312 is further formed so that an annular groove 320 extends circumferentially around head 318. Groove 320 is arcuate in cross section. The input spindle 312 is shaped so that when the spindle head 318 seats in output spindle bore 204, ball bearings 205 will seat in groove 320.

The input spindle 312 is further formed so as to have a bore 322 that extends proximally from the distally directed face of spindle base 314. Bore 322 is dimensioned to press fit receive shaft stem 294. The base 314 is further formed to have two coaxial openings 324. Openings 324 each open into bore 322.

When the cup remover 30 is assembled, the input spindle base 312 is press fit over shaft stem 294. A pin 326, seen only in FIGS. 2B and 41, extends through spindle openings 324 and shaft bore 296 to further hold the shaft 292 and input spindle 312 together.

Figure 29:
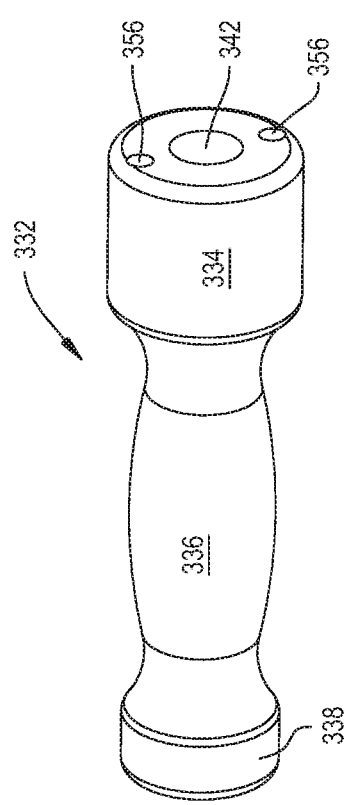
FIG. 29 is a perspective view of the handle of the cup remover.
Figure 30:
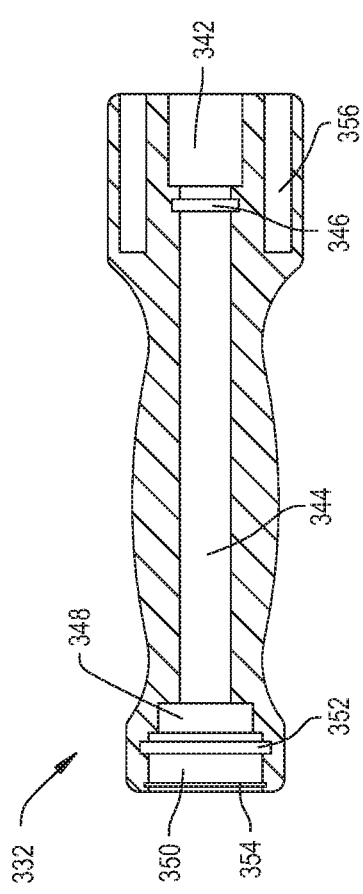
FIG. 30 is a cross sectional view of the handle of FIG. 29.

Handle 332, now described by reference to FIGS. 29 and 30, is slidably disposed over both the proximal portion of shaft 292 and the base 314 of the input spindle 312. The handle 332 is a single piece component that, like essentially all components forming the cup remover 30, can be subjected to autoclave sterilization. The handle 332 is generally in the form of a tube. The handle is shaped to have a head 334 that has a generally constant outer diameter. Head 334 is the most proximally located portion of the handle 332. A trunk 336 extends distally from head 334. The trunk has a varying outer diameter. Specifically, the trunk is shaped to ergonomically receive the palm of the hand and fingers of the individual using cup remover 30. A base 338 forms the distalmost portion of handle 332. The base 338 has a constant outer diameter. In the illustrated version of the invention, the diameter of base 338 is less than that of head 334.

A set of bores extend axially through the handle 332. A first bore, bore 342, extends distally forward from the proximally directed face of the head 334. Bore 342 extends partially through the head 334. Bore 342 is dimensioned to slidingly receive the base 314 of the input spindle 312. Bore 342 opens up into a bore 344. Bore 344 extends through the distal portion of the head 334 and most of the trunk 336. Bore 344 has a diameter less than that of bore 342. The bore 344 is dimensioned to slidably receive shaft 292. Adjacent bore 342 a groove 346 extends outwardly from the cylindrical inner wall of handle 332 that defines bore 344. The distal end of bore 344 opens into a bore 348. Bore 348 extends through the most distal portion of the trunk and the adjacent proximal section of the base 338. Bore 348 has a diameter greater than that of bore 344. Bore 348 opens into a bore 350 which is the distalmost bore of the handle 332. Bore 350 extends from bore 348 to the distally directed face of the handle 332. Bore 350 has a diameter greater than that of bore 348. The handle 332 is further formed so that two grooves, grooves 352 and 354, extend outwardly from inner wall of the handle that defines bore 350. Groove 352 is proximal to bore 348. Groove 354 is proximal to the distal end of the handle 332. Groove 352 is greater in diameter and length than groove 354.

The handle 332 is formed to have two additional bores, closed end bores 356. Bores 356 extend inwardly from the proximally directed face of the handle 332. Bores 356 are diametrically opposed from each other. Bores 356 are parallel to and spaced apart from the adjacent bore 342. Bores 356 are dimensioned and positioned so that when the cup remover 30 is attached to driver 50, each driver pin 262 slidably seats in a separate one of the bores 356.

Figure 32:
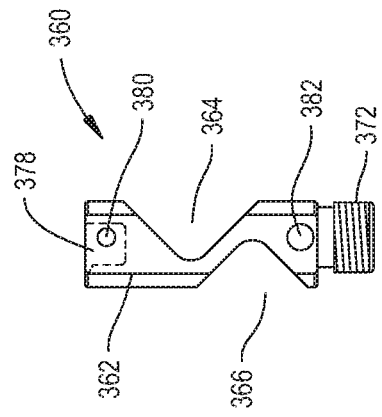
FIG. 32 is a perspective view of the head-to-shaft coupler between the shaft and the pivot head.
Figure 33:
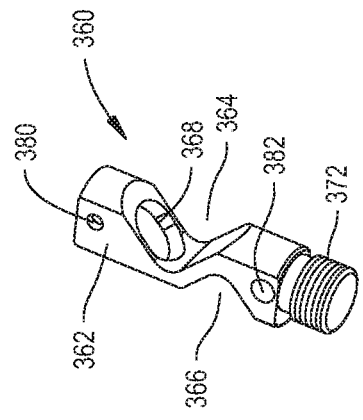
FIG. 33 is a side plan view of the coupler of FIG. 32.

A static head-to-shaft coupler 360, now described by reference to FIGS. 32 and 33, is the component that holds cup remover head 388 to the distal end of shaft 292. Coupler 360 is formed as a single piece component. The coupler has a stem 362. In one version of the invention the stem 362 has flat parallel side surfaces. Front and rear surfaces that convex in shape extend between the side surface (individual surfaces not identified). The stem 362 is formed to define two V-shaped indentations 364 and 366. The indentations 364 and 366 extend inwardly from the opposed front and rear surfaces. The indentation 364 is the proximal of the two indentations. The stem is further formed so that the proximalmost diagonal face that defines indentation 364 is formed to have a recess 368.

Forward of stem 362, coupler 360 has a cylindrical head 372. Not identified is the neck with a diameter less than that of the head 372 between the stem 362 and the head. Head 372 is formed with threading, not identified on the outer circumferential surface.

A closed end bore 378, shown in dashed lines only in FIG. 33, extends forward from the distal end of stem 362. Bore 378 is dimensioned to press fit receive shaft head 306. A bore 380 extends through the opposed side faces of the stem 362. Bore 380 intersects bore 378. When the cup remover 30 is assembled, shaft head 306 is seated in coupler bore 378. A pin 382, seen only in FIG. 2B, extends through the coaxial head bore 306 and coupler bore 380 further holds the coupler 360 to the shaft. Coupler 360 is further formed to have a second bore, bore 382, that extends side-to-side through stem 362. Bore 382 is located proximal to the distal end of the stem 362.

The pivot head 388, as seen in FIG. 34, has a distal facing surface 390. Surface 390 is designed to be seated in the inner surface of the acetabular cup 32 cup remover 30 is intended to remove. Surface 392 is generally in the form of a slice section of a sphere. Pivot head 388 has a distal facing surface 392 opposite surface 390. Surface 392 is generally planner. A ring-shaped fitting 394 is mounted to head 388 so as to extend inwardly from surface 390. Fitting 394 defines a close end bore 396. Fitting 394 is formed with threading, not seen, around bore 396 so the bore can receive coupler head 372.

Blade 402, now described by reference to FIG. 35, includes a body 404. Specifically, in some versions of the invention the body 404 has a proximal section, (not identified). Extending from the proximal section there is a distal section (not identified) that is curved. The body distal section is formed with teeth 406.

The blade 402 is further formed to have a tab 408 that extends perpendicularly away from the proximal section of the body 404. Tab 408 is in the form of a rectangular beam. In the depicted version of the invention, the distal section of the body is formed with an opening 410. An end section of the tab 408 is welded or otherwise secured in the opening 410. Tab 408 is shaped to have a closed end bore 412, (shown in phantom). Bore 412 extends inwardly from the proximally directed surface of tab 408.

A hinge 418, seen best in FIGS. 36 and 37, pivotally connects the blade 408 to coupler 360. The hinge 418 includes a base 420 that is approximately rectangular in shape. Base 420 includes top located side surfaces that are inwardly tapered toward each other (surfaces not identified). Two parallel legs 422 project outwardly from one end of the base 420. Hinge 418 is spaced so that the legs 422 can slip fit over the opposed parallel flat surfaces of the coupler stem 362. Each leg 422 is formed so as to have a rounded free end (not identified).

The hinge 418 is formed that a rectangular slot 426 extends through base 420. The longitudinal axis of slot 426 is parallel to the longitudinal axes of legs 422. Slot 426 is dimensioned to receive the tab 408 integral with the blade 402. An opening 428 extends through the top portion of hinge base 418. Opening 428 extends to slot 426. Coaxial openings 430 (one shown) extend through the opposed sides of the hinge 418 where the legs 422 extend from the base 420. Each opening 430 partially intersects the base 420. The face of the base adjacent is formed with two grooves 431 (one shown). Each groove 431 has a radius of curvature equal to the radius of the openings 430 and has a curve that is centered on the common axes through openings 430. Each leg 422 is formed with a through hole 423. Leg through holes 423 are coaxial.

The assembly that removably holds blade 402 to hinge 418, seen in FIG. 37, includes a sleeve like bushing 432. Bushing 432 is press fit in hinge opening 428. A lock pin 434 is disposed in bushing 432 to move up and down within the bushing. Lock pin 434 has a tip 436 designed to seat in bore 412 integral with blade 402. Above the tip 436 the lock pin 434 has a lip 438 that protrudes radially outwardly and circumferentially around the main body of the tip 436. A ring-shaped retainer 452 is press fit into the end of bushing 432 spaced from the hinge 418. The components are further dimensioned so that the end of the lock pin 434 opposite tip 436 protrudes above retainer 452.

A helical spring 450 is disposed around the main body of the lock pin 434. Spring 450 extends between the static inner surface of retainer 452 and lip 438 integral with the lock pin 434. The spring 450 places a force on the lock pin 434 that tends to hold the pin tip 436 in hinge slot 426. The end of the pin 434 opposite the tip 436, the section that extends above retainer 452, is attached to a button 454. In the absence of another force, spring 450 holds button 454 over bushing 432. This coupling assembly is moved from the run state to the load state by pulling outwardly on button 454. This manual force overcomes the force spring 450 applies to the pin 434 so as to hold tip 436 in the hinge slot 426.

Upon assembly of the cup remover 30, hinge 418 is positioned so that each leg through hole 423 is adjacent a separate one of the openings into coupler bore 382. A pin 460 extends through hinge holes 423 and coupler bore 382 to statically hold the hinge 418 to coupler 360.

Figure 38:
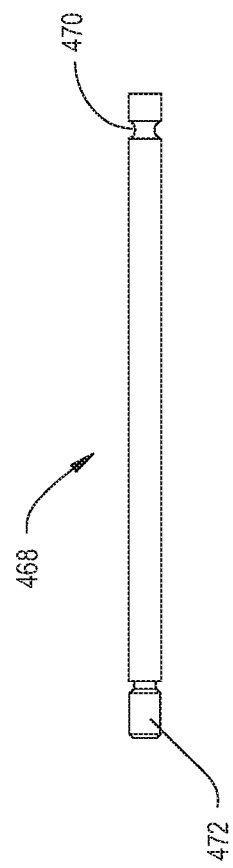
FIG. 38 is a plan view of the actuator rod.

An actuator rod 468 and an actuator 502 connect the handle 332 to hinge 416. Actuator rod 468, now described by reference to FIG. 38, is an elongated solid cylindrical rod. The rod 468 has a diameter that facilitates the seating of the rod in shaft groove 302. While rod 468 can seat in groove 302, the rod is shorter in length than the groove. Slightly forward of the proximal end, rod 468 is shaped to have a groove 470. Groove 470 is concave in shape and extend circumferentially around the rod 468. The actuator rod 468 is further formed to have at the distal end a head 472. Not identified is the undercut neck between the main body of the rod 468 and head 472.

Figure 31:
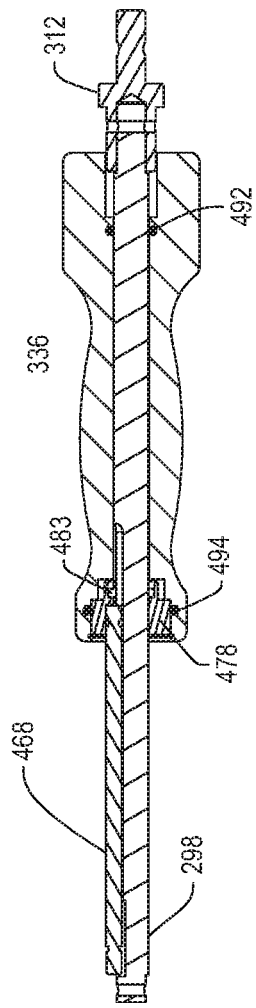
FIG. 31 is a cross sectional view of the handle depicting the components in the handle.

When cup remover 30 is assembled, the actuator rod 468 is slidably disposed in shaft groove 302. A lock ring 478, seen best in FIGS. 31 and 39, holds the actuator rod 468 to the handle 332. Lock ring 478 is generally cylindrical in shape. The lock ring is formed to have a proximally directed head 479. Head 479 has an outer diameter less than that of the main body of the lock ring 478. The lock ring 478 is formed to define a bore 480 that is circular in cross section and coaxial with the proximal-to-distal longitudinal axis through the lock ring, including head 479. Bore 480 is dimensioned to receive shaft 292. Lock ring 478 is further shaped to define a groove 482 that extends inwardly from the inner wall of the ring that defines bore 480. Groove 482 is shaped such that when the shaft 292 and rod 468 are seated in the lock ring, the portion of the rod 468 that extends above the shaft seats in groove 482. Groove 482 extends proximally from the distally directed face of the lock ring. The groove 482 does not extend into the proximally located head portions 479 of the ring 478. Thus, a step 483 internal to the lock ring defines the proximal end of groove 482.

A bore 484 extends laterally through a portion of the lock ring 478. Here laterally is understood to be in a plane perpendicular to the longitudinal axis through the lock ring. Bore 484 is located so as to intersect the base of groove 482.

When the cup remover 30 is assembled, shaft 292 seats in bore 480. Actuator rod 468 seats in lock ring groove 482. The proximal end of the rod is disposed against step 483 internal to the lock ring 478. Actuator rod 468 is thus positioned so that the rod groove 470 is in registration with lock ring groove 482. A pin 486 seen only in FIG. 2A, extends through lock ring groove 482 and actuator rod groove 470 to hold the actuator rod in a static position relative to the lock ring 478.

Lock ring 478 is rotatably mounted in handle bore 350. Lock ring head 479 is disposed in bore 348. A snap ring 488, seen in FIG. 2A, seated in handle groove 354 holds the lock ring in bore 350. When the cup remover 30 is assembled an O-ring 492 is disposed in handle groove 346. The O-ring 492 is disposed around shaft 292. An O-ring 494 is seated in handle groove 352. The O-ring 494 is compressed between the handle 332 and the outer surface of lock ring 478. The O-rings 492 and 494 function as seals that minimize the flow of liquids and vapors into the handle 332.

Actuator 502, as seen best in FIG. 40, is a single piece unit. The actuator includes a foot 504. Foot 504 is generally rectangular in shape. The foot 504 is dimensioned to seat on and not extend laterally outwardly of shaft flat 304. A leg 506 extends forward from one side of the foot 504. The leg 506 is in the form of a rectangular bar. Leg 506 has a width less than that of foot. Foot 504 and leg 506 share a single common planar face. A step 508 projects laterally away from the distal end of leg 506. A head 510 extends forward from step 508. Actuator head 510 is generally in the form of a right triangle with rounded corners. One of the right-angle forming sides of the head is parallel with the proximal-to-distal longitudinal axis along leg 506. The second right angle forming side of the head is perpendicular to this longitudinal axis and is immediately adjacent step 508.

A bore 512 seen in phantom extends from the proximal end of actuator foot 504. Bore 512 is shaped to receive actuator rod head 472. The actuator 502 is further formed so as to have a slot 514 in head 510. Slot 514 is located inwardly of the surface of the head that defines the triangle defined by the head 510. Thus, from the most portion of the slot 514, the slot extends diagonally proximally away and away from longitudinal axis of the actuator leg 506.

Actuator 502 is positioned so that foot 504 is disposed over shaft flat 304 and leg 506 extends over one of the outer flat side surface of coupler 360. The head 472 of actuator rod 468 is threaded in actuator bore 472, (threading not shown). A pin 516 connects the actuator 502 to hinge 418. Pin 516 extends through slot 514 internal to the actuator and coaxial openings 430 and groove 431 integral with the hinge 418. The head of pin 516 (pin head not identified) is disposed over the outer surface of the portion of the actuator head 510 that defines slot 514. The pin 516 thus performs two functions. The pin 516 connects the hinge 418 to the actuator 502. Pin 516 also extends across the rear opening of hinge slot 426. The pin thus also limits the movement of the blade tab 408 in the slot. More particularly, when the blade tab 408 is disposed against pin 516, tab bore 412 is positioned to receive lock pin tip 436.

IV. Operation

Cup remover 30 of this invention is prepared for use by first fitting the blade 402 to hinge 418. This is accomplished by pulling up on button 454. The manual force on applied to the button overcomes the force of spring 450 that holds pin tip 436 in hinge slot 426. Once the pin tip is retracted away from the hinge slot 426, blade 402 is mounted to the hinge by seating the blade tab 408 in hinge slot 426. Once the blade tab bore 412 is in registration with the pin 434, button 454 is released. The force spring 450 applied to lock pin 434 hold the pin tip 436 in blade tab bore 412. The blade is thus removably coupled to the hinge 414.

The cup remover 30 is then coupled to driver 50. This is accomplished by pulling retainer 236 proximally over the eccentric housing 108. Manual force is all that is required to overcome the force spring 266 applies to the retainer 236 so as to hold the retainer away from driver housing 52. The longitudinal displacement of the retainer 236 results in the retainer moving so that the bearings 268, instead of being disposed in retainer bore 252, are disposed in retainer bore 256. Bore 256 is larger in diameter than bore 252. The ball bearings 205 are thus free to move laterally out of the spindle bores 204 and into the annular space between the outer surface of the output spindle and adjacent bore 256-defining surface of the retainer. At this time the driver 50 can be considered in the state in which the cup remover 30 can be loaded to the driver.

Figure 41:
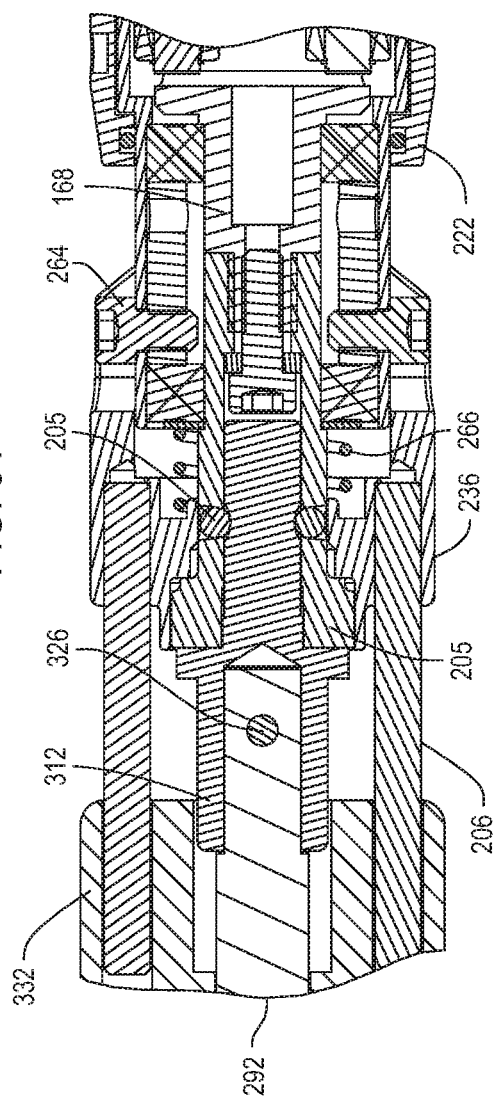
FIG. 41 is a cross sectional of how the cup remover is removably attached to the driver.

The cup remover coupling process continues with the fitting of the cup remover 30 so that each one of the pins 262 integral with retainer 236 seat in a separate one of the handle bores 356 as seen in FIG. 41. The cup remover 30 and driver 50 are brought further together so that the input spindle neck 318 seats in notch 196 integral with output spindle 184. This process may require the rotation of the output spindle 184 to place the neck 318 in alignment with the output spindle notch 196. Once the spindles are so positioned, groove 320 integral with the input spindle 312 is in registration with openings 201 integral with the output spindle 184. The force holding the retainer 236 in the load position is released. Spring 266 pushes the retainer 236. As a consequence of this displacement of the retainer, bearings 205 are pressed against the annular wall of the retainer that defines bore 256. The retainer thus pushed the bearings 205 inwardly into the output spindle bore 204. More specifically, the bearings seat in the groove 320 integral with the input spindle 312. The driver 50 is in a state in which the cup remover 30 is releasably locked to the driver.

Cup remover 50 is used by positioning the pivot head 388 in the socket of the acetabular cup 32 the remover is being used to remove. The surgeon holds the driver handle 62 in one hand and the cup remover handle 332 in the other hand. Blade 402 is pressed against the bone adjacent the outer surface of cup 32 by pushing the cup remover handle distally, towards pivot head 388. This results in a like movement of the actuator rod 468 and, by extension, actuator 502. The resultant like movement of pin 516 causes hinge 418 to pivot outwardly. The outward pivoting of the hinge 418 combined with the curved shape of blade 402 forces the blade against the outer surface of the cup 32.

The surgeon oscillates the blade 402 against a section of bone by depressing trigger 84. This results in the actuation of the motor 68 so as to rotate shaft 70. The rotation of shaft 70 results in the like simultaneous rotation of the eccentric shafts 136. Specifically, each eccentric shaft 136 rotates around common access of the shaft foot 138 and leg 140. The shaft head 146 rotates around this same axis. Since the shaft head is off axis with this axis, the shaft head 146 is understood to rotate in a circular motion around this axis. The movement of the shaft heads 146 is captured by the link 168 disposed over the eccentric shaft heads 146. Owing to the arrangement of these components, this movement results in the link engaging an oscillator rotation around the common axis of the link head 176 and nose 178.

The oscillator motion of the link 168 is transferred by the output spindle 184, the input spindle 312, shaft 292 to link 360. The oscillation of link 360 results the like oscillation of hinge 418 and, therefore, blade 402 around the axis of shaft 292. Blade 402 is thus oscillated back and forth against the bone the blade is positioned to cut.

In some versions of the invention, blade 402 oscillates over an arc between 15 and 2°. In still other versions of the invention, blade 402 oscillates over an arc between 8 and 5°.

Once the blade 402 is used to form a cut in some bone, cup remover 30 is designed allow the rotation, the indexing, of the blade, so the blade can remove another section of bone. This step is performed by rotating handle 332. The rotation of the handle 332 is, through pins 262, transferred to retainer 236. The rotation of the retainer 236 is, through screws 264, transferred to the eccentric housing 108. During this process it is understood that the eccentric housing base 110 rotates against the inner surface of the cup insert main body 93. Owing to the materials from which the cup insert 92 and eccentric housing 108 are formed these components are essential their own low friction bearing. The resultant rotation of the eccentric housing 108 results in the rotation of the rotational positions of the eccentric shafts 136 relative to the motor shaft 70. In other words, the eccentric shafts 136 rotate around the fixed axis of the motor shaft 70.

The rotation of the eccentric shafts 136 result in a like rotation of the eccentric shaft heads 146. The rotation of the eccentric shaft heads causes the surrounding plates 170 to undergo a like rotation. This rotation of the eccentric plates 170 causes the link to rotate around the axis that extends through the link head 176. As described above, rotational movement of the link head 176 results in the same movement of the blade 402. Blade 402 is thus rotated to a new rotational position relative to a fixed axis that extends from longitudinally along cup remover shaft 292. This axis also extends from driver 50. By again depressing on the handle 332 and actuating the motor 68, the blade 402 can cut the new section of bone against which the base has been positioned.

Cup remover 30 of this invention is thus designed so that, once seated in a cup 32, blade 402 can be rotated a complete 360° to be worked all of the bone against which the cup is embedded. Blade 402 can be so repositioned without having to shift the position of the driver 50 relative to a static axis that extends from the cup. Thus, once the surgeon establishes a comfortable orientation for holding the driver relative to the cup 32, there is no need to reorient the driver 50 to ensure the blade is cycled completely around the cup.

A further feature of this invention is that the orientation of the blade 402 is reset without having to remove and then reinsert the pivot head 388 in the cup 32. Thus, the effort associated with this indexing operation does not appreciable add to the overall time required to remove the cup.

V. Alternative Embodiments

The above is directed to one specific version of the cup remover of this invention. Other versions of the cup remover may have features different from what has been described.

For example, in the disclosed version of the invention a number of components perform multiple functions. There is no requirement that this functionality be present in all versions of the invention. Specifically, the described retainer 236 performs functions associated with: the removably coupling of the cup remover to the driver; the oscillation of the cup remover; and the indexing of the blade. In alternative versions of the invention the retainer may perform only one or two of these functions.

Thus, an alternative version of the invention may have a transmission that does nothing other than convert the rotational movement of a motor shaft into a motion that oscillates the blade back and forth. A coupling assembly with separate components may removably hold the cup remover to the transmission. A third unit may perform the indexing function that rotates the blade around the fixed axis extending from the cup 32. This third unit, the indexing assembly, may be either part of the driver or part of the cup remover. Alternatively, this third unit that performs the indexing, the rotation of the blade 402 around shaft 292 may be separate from the coupling assembly and the transmission assembly.

Likewise, not all features be present in all versions of the invention. For example, in some versions of the invention, there may not be a coupling unit that removably holds the components distal to the driver 50 to the driver. In these versions of the invention, only the blade may be removably attached to the rest of the invention.

Further, other versions of this invention may include other assemblies. For example, an alternative cup remover of this invention may have two shafts, for example, an inner and an outer shaft. The inner shaft extends to the pivot head and serves primarily as a support to hold the other components of the cup remover away from the pivot head. The outer shaft is rotatably and slidably disposed over the inner shaft. The hinge is pivotally attached to the outer shaft. In these versions of the invention, the outer shaft is moved longitudinally along the inner shaft to pivot the blade assembly and rotated around the inner shaft to index the blade assembly.

In some versions of the invention, additional low friction bearing components may function as the interface between the static cup insert 92 and the eccentric housing 108. This "component" may be a lubricant or coating.

It should likewise be understood that the size and shape of the head 388 and the size and shape of the blade 402 are a function of the characteristics of the cup 32 that is be removed.

Further there may be versions of the invention configured so that actuator rod and actuator are likewise able to rotate around the shaft. In these versions of the invention, the rotation of the handle 332 is directly transferred from the handle to the actuator rod. The rotation of the actuator rod in turn is applied to the hinge so as to result in a like rotation of the hinge and blade. An advantage of this version of the invention is that the transmission components associated with the drive needed not also be designed to engage in the rotation associated with the indexing operation.

In the described version of the invention the driver including the coupling features integral with the driver 50 to hold the cup remover to the driver are specifically designed for use with the cup remover. This may not be the case with all versions of the invention. It is contemplated that a cup remover of this invention may be designed to work with a driver that performs other functions. One such driver is described in U.S. Pat. Pub. No. 2007/0021766 A1, SURGICAL HANDPIECE WITH COMPACT CLUTCH AND ANTI-WOBBLE COUPLING HEAD, the contents of which are incorporated herein by reference. This handpiece, sometimes referred to as a heavy-duty driver, includes a rotating spindle. The spindle is shaped to receive surgical instruments in addition to the cup remover of this invention. One such instrument is the shaft of a reamer. An electric circuit internal to this heavy-duty driver is able to oscillate the spindle. Thus, a cup remover of this invention designed to work with this type of driver may include a coupling assembly designed to hold the shaft to the driver spindle, an assembly for indexing, rotating, the blade around the static axis through the pivot head, and an assembly for pivoting the blade.

Given the above it should be appreciated that some drivers of this invention may not rely on a mechanical transmission to convert the rotational motion energy of a motor shaft into an oscillatory motion. Other mechanical transmissions such as a transmission that includes single eccentric shaft be employed. Further, the motor shaft may not rotate. As discussed above, a control circuit may regulate the application of energization signals to the motor shaft so that the shaft only oscillates. In this version of the invention, the transmission may be a step-down assembly that converts 180 to 540° of motor shaft rotation in one phase into 5 to 15° of blade movement.

Further, some cup removers of this invention may have two handles. The practitioner manipulates one handle to regulate the pivoting of the blade. The second handle is part of the indexing assembly and is manipulated to set the rotational orientation of the blade. This two-handle version of the invention may be appropriate so that when the surgeon moves to pivot the blade the blade is not inadvertently rotated. this design also prevents the surgeon from inadvertently pivoting the blade when all that the surgeon wants to perform is a rotational shift.

The pivot head 388 may be shaped to be received in a liner within a cup 32. Some pivots are shaped to be received against the inner surface of the cup 32. This inner surface may be the exposed inner surface of the shell once the liner is removed.

Also, while this invention is designed as an acetabular cup remover, the invention may have other applications. For example, after a pilot hole is drilled in tissue, an alternative version of this invention could be used to form a socket in the tissue.

The invention may have additional applications beyond medicine and surgery.

Accordingly, it is an object of the appended claims to cover all such modifications and variations as come within the true spirit and scope of this invention.

What is claimed is:

1. A method of indexing an acetabular cup remover, the method comprising:
   providing an acetabular cup remover assembly comprising a powered surgical driver and an acetabular cup remover coupled to the powered surgical driver, the acetabular cup remover comprising a shaft having a longitudinal axis that extends distally to proximally through the shaft; a blade disposed adjacent a distal end of the shaft that is shaped to extend around an acetabular cup, wherein the blade is configured to pivot about a pivot axis that is transverse to the longitudinal axis;
   positioning the acetabular cup remover against the acetabular cup with the blade in a first radial orientation relative to the longitudinal axis and the powered surgical driver;
   displacing the blade to force the blade against a section of bone adjacent the acetabular cup of a patient;

actuating the powered surgical driver with the blade in the first radial orientation to oscillate the shaft to oscillate the blade to form a first arcuate cut into the bone;

rotating the blade about the longitudinal axis to a second radial orientation relative to the longitudinal axis and the powered surgical driver without disconnecting the shaft from the powered surgical driver; and actuating the powered surgical driver with the blade in the second radial orientation to oscillate the shaft to oscillate the blade to form a second arcuate cut into the bone.

2. The method of claim 1, wherein the acetabular cup remover further comprises a handle slidably coupled to the shaft, the method further comprising sliding the handle along the longitudinal axis to displace the blade.

3. The method of claim 2, further comprising rotating the handle about the longitudinal axis relative to the powered surgical driver without disconnecting the shaft from the powered surgical driver to rotate the blade about the longitudinal axis.

4. The method of claim 1, wherein the driver comprises a drive shaft, the method further comprising rotating the drive shaft about the longitudinal axis in response to the actuation of the surgical driver to oscillate the shaft to oscillate the blade to form cuts into the bone.

5. The method of claim 4, wherein the acetabular cup remover assembly further comprises an eccentric shaft disposed in meshing relationship with the drive shaft, the method further comprising rotating the eccentric shaft about an eccentric shaft axis parallel to the longitudinal axis in response to the rotation of the drive shaft to oscillate the shaft to oscillate the blade to form the cuts into the bone.

6. The method of claim 5, wherein the rotation of the blade about the longitudinal axis without disconnecting the shaft from the powered surgical driver comprises revolving the eccentric shaft around the longitudinal axis.

7. A method of indexing an acetabular cup remover, the method comprising:

providing an acetabular cup remover assembly comprising a powered surgical driver and an acetabular cup remover coupled to the powered surgical driver, the acetabular cup remover comprising a shaft having a longitudinal axis that extends distally to proximally through the shaft; a blade disposed adjacent a distal end of the shaft that is shaped to extend around an acetabular cup, wherein the blade is configured to pivot about a pivot axis that is transverse to the longitudinal axis;

positioning the acetabular cup remover against the acetabular cup with the blade in a first radial orientation relative to the longitudinal axis and the powered surgical driver;

displacing the blade to force the blade against a section of bone adjacent the acetabular cup of a patient;

actuating the powered surgical driver with the blade in the first radial orientation to oscillate the shaft to oscillate the blade to form a first arcuate cut into the bone;

rotating the blade about the longitudinal axis to a second radial orientation relative to the longitudinal axis and the powered surgical driver while the shaft is connected to the powered surgical driver; and actuating the powered surgical driver with the blade in the second radial orientation to oscillate the shaft to oscillate the blade to form a second arcuate cut into the bone.

8. The method of claim 7, wherein the acetabular cup remover further comprises a handle slidably coupled to the shaft, the method further comprising sliding the handle along the longitudinal axis to displace the blade.

9. The method of claim 8, further comprising rotating the handle about the longitudinal axis relative to the powered surgical driver while the shaft is connected to the powered surgical driver to rotate the blade about the longitudinal axis.

10. The method of claim 7, wherein the driver comprises a drive shaft, the method further comprising rotating the drive shaft about the longitudinal axis in response to the actuation of the surgical driver to oscillate the shaft to oscillate the blade to form cuts into the bone.

11. The method of claim 10, wherein the acetabular cup remover assembly further comprises an eccentric shaft disposed in meshing relationship with the drive shaft, the method further comprising rotating the eccentric shaft about an eccentric shaft axis parallel to the longitudinal axis in response to the rotation of the drive shaft to oscillate the shaft to oscillate the blade to form the cuts into the bone.

12. The method of claim 11, wherein the rotation of the blade about the longitudinal axis while the shaft is connected to the powered surgical driver comprises revolving the eccentric shaft around the longitudinal axis.

* * * * *